US009215989B2

(12) United States Patent
Kaib et al.

(10) Patent No.: US 9,215,989 B2
(45) Date of Patent: Dec. 22, 2015

(54) WEARABLE AMBULATORY MEDICAL DEVICE WITH MULTIPLE SENSING ELECTRODES

(71) Applicant: ZOLL MEDICAL CORPORATION, Chelmsford, MA (US)

(72) Inventors: Thomas E. Kaib, North Huntingdon, PA (US); Shane Volpe, Saltsburg, PA (US); John D. Macho, Farmington, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/245,636

(22) Filed: Apr. 4, 2014

(65) Prior Publication Data
US 2014/0336519 A1   Nov. 13, 2014

Related U.S. Application Data

(63) Continuation of application No. 13/109,382, filed on May 17, 2011, now Pat. No. 8,706,215.

(60) Provisional application No. 61/424,344, filed on Dec. 17, 2010, provisional application No. 61/345,914, filed on May 18, 2010.

(51) Int. Cl.
*A61B 5/04* (2006.01)
*A61B 5/0452* (2006.01)
(Continued)

(52) U.S. Cl.
CPC ........... *A61B 5/0452* (2013.01); *A61B 5/04085* (2013.01); *A61B 5/6805* (2013.01);
(Continued)

(58) Field of Classification Search
USPC ...................................... 607/5; 600/509–510
See application file for complete search history.

(56) References Cited

U.S. PATENT DOCUMENTS

| 4,094,310 A | 6/1978 | McEachern et al. |
| 4,632,122 A | 12/1986 | Johansson et al. |

(Continued)

FOREIGN PATENT DOCUMENTS

| CN | 101019761 A | 8/2007 |
| CN | 201394012 Y | 2/2010 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ full/166/1/111.
DeBock, et al., "Captopril treatment of chronic heart failure in the very old," J. Gerontol. (1994) 49: M148-M152.
International Search Report and Written Opinion from corresponding International Application No. PCT/US2011/036805, dated Aug. 26, 2011.

(Continued)

*Primary Examiner* — Nicole F Lavert
(74) *Attorney, Agent, or Firm* — Lando & Anastasi, LLP

(57) ABSTRACT

An ambulatory medical device including a plurality of electrodes configured to be disposed at spaced apart positions about a patient's body, an electrode signal acquisition circuit, and a monitoring circuit. The acquisition circuit has a plurality of inputs each electrically coupled to a respective electrode of the plurality of electrodes and is configured to sense a respective signal provided by a plurality of different pairings of the plurality of electrodes. The monitoring circuit is electrically coupled to an output of the acquisition circuit and is configured to analyze the respective signal provided by each of the plurality of different pairings and to instruct the acquisition circuit to select at least one of the plurality of different pairings to monitor based on at least one of the quality of the respective signal, a phase difference between the respective signal and that of other pairings, a position of electrodes relative to the patient's body, and other criteria.

23 Claims, 15 Drawing Sheets

(51) Int. Cl.

| | |
|---|---|
| *A61B 5/0408* | (2006.01) |
| *A61N 1/04* | (2006.01) |
| *A61B 5/00* | (2006.01) |
| *A61B 5/021* | (2006.01) |
| *A61B 5/053* | (2006.01) |
| *A61B 5/08* | (2006.01) |
| *A61B 5/11* | (2006.01) |
| *A61B 5/145* | (2006.01) |
| *A61N 1/39* | (2006.01) |

(52) U.S. Cl.
CPC ............ *A61B5/7207* (2013.01); *A61B 5/7221* (2013.01); *A61N 1/046* (2013.01); *A61N 1/0484* (2013.01); *A61N 1/3987* (2013.01); *A61B 5/0006* (2013.01); *A61B 5/021* (2013.01); *A61B 5/053* (2013.01); *A61B 5/0816* (2013.01); *A61B 5/11* (2013.01); *A61B 5/14542* (2013.01); *A61N 1/39* (2013.01)

(56) References Cited

U.S. PATENT DOCUMENTS

| | | | |
|---|---|---|---|
| 4,928,690 A | 5/1990 | Heilman et al. | |
| 4,978,926 A | 12/1990 | Zerod et al. | |
| 5,062,834 A | 11/1991 | Gross et al. | |
| 5,078,134 A | 1/1992 | Heilman et al. | |
| 5,184,620 A | 2/1993 | Cudahy et al. | |
| 5,348,008 A | 9/1994 | Bornn et al. | |
| 5,365,932 A | 11/1994 | Greenhut | |
| 5,381,798 A | 1/1995 | Burrows | |
| 5,472,453 A | 12/1995 | Alt | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,827,196 A | 10/1998 | Yeo et al. | |
| 5,887,978 A | 3/1999 | Lunghofer et al. | |
| 5,929,601 A | 7/1999 | Kaib et al. | |
| 5,944,659 A | 8/1999 | Flach et al. | |
| 5,944,669 A | 8/1999 | Kaib | |
| 6,016,445 A | 1/2000 | Baura | |
| 6,045,503 A | 4/2000 | Grabner et al. | |
| 6,065,154 A | 5/2000 | Hulings et al. | |
| 6,097,982 A | 8/2000 | Glegyak et al. | |
| 6,097,987 A | 8/2000 | Milani | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,301,502 B1 | 10/2001 | Owen et al. | |
| 6,390,996 B1 | 5/2002 | Halperin et al. | |
| 6,406,426 B1 | 6/2002 | Reuss et al. | |
| 6,681,003 B2 | 1/2004 | Linder et al. | |
| 6,687,523 B1 | 2/2004 | Jayaramen et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,990,373 B2 | 1/2006 | Jayne et al. | |
| 7,149,579 B1 | 12/2006 | Koh et al. | |
| 7,220,235 B2 | 5/2007 | Geheb et al. | |
| 7,340,296 B2 | 3/2008 | Stahmann et al. | |
| 7,453,354 B2 | 11/2008 | Reiter et al. | |
| 7,488,293 B2 | 2/2009 | Marcovecchio et al. | |
| 7,712,373 B2 | 5/2010 | Nagle et al. | |
| 7,831,303 B2 | 11/2010 | Rueter et al. | |
| 7,974,689 B2 | 7/2011 | Volpe et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 2003/0004547 A1 | 1/2003 | Owen et al. | |
| 2003/0095648 A1 | 5/2003 | Kaib et al. | |
| 2003/0149462 A1 | 8/2003 | White et al. | |
| 2003/0158593 A1 | 8/2003 | Heilman et al. | |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2004/0049233 A1 | 3/2004 | Edwards | |
| 2005/0049515 A1 | 3/2005 | Misczynski et al. | |
| 2005/0131465 A1 | 6/2005 | Freeman et al. | |
| 2006/0036292 A1 | 2/2006 | Smith et al. | |
| 2006/0085049 A1 | 4/2006 | Cory et al. | |
| 2006/0178706 A1 | 8/2006 | Lisogurski et al. | |
| 2006/0270952 A1 | 11/2006 | Freeman et al. | |
| 2007/0118056 A1 | 5/2007 | Wang et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0265671 A1 | 11/2007 | Roberts et al. | |
| 2007/0293774 A1* | 12/2007 | Acquista ...................... 600/509 |
| 2008/0004536 A1 | 1/2008 | Baxi et al. | |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058884 A1 | 3/2008 | Matos | |
| 2008/0249591 A1 | 10/2008 | Gaw et al. | |
| 2008/0306560 A1 | 12/2008 | Macho et al. | |
| 2008/0312709 A1 | 12/2008 | Volpe et al. | |
| 2009/0018428 A1 | 1/2009 | Dias et al. | |
| 2009/0069678 A1 | 3/2009 | Taniyama et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0093687 A1 | 4/2009 | Telfort et al. | |
| 2009/0138059 A1 | 5/2009 | Ouwerkerk | |
| 2009/0234410 A1 | 9/2009 | Libbus et al. | |
| 2009/0264792 A1 | 10/2009 | Mazar | |
| 2009/0275848 A1 | 11/2009 | Brockway et al. | |
| 2009/0281394 A1 | 11/2009 | Russell et al. | |
| 2009/0287120 A1 | 11/2009 | Ferren et al. | |
| 2009/0292194 A1 | 11/2009 | Libbus et al. | |
| 2010/0041975 A1 | 2/2010 | Chen et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0234716 A1 | 9/2010 | Engel | |
| 2010/0295674 A1 | 11/2010 | Hsieh et al. | |
| 2010/0298899 A1 | 11/2010 | Donnelly et al. | |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0146797 A1 | 6/2012 | Oskin et al. | |
| 2012/0150008 A1 | 6/2012 | Kaib et al. | |
| 2012/0158075 A1 | 6/2012 | Kaib et al. | |

FOREIGN PATENT DOCUMENTS

| | | |
|---|---|---|
| EP | 0295497 B1 | 9/1993 |
| EP | 0335356 B1 | 3/1996 |
| EP | 1455640 B1 | 1/2008 |
| EP | 1720446 B1 | 7/2010 |
| JP | 5115450 A | 5/1993 |
| JP | 2002514107 A | 5/2002 |
| JP | 2002159458 A | 6/2002 |
| JP | 2007500549 A | 1/2007 |

(56) References Cited

FOREIGN PATENT DOCUMENTS

| | | |
|---|---|---|
| WO | 0002484 A1 | 1/2000 |
| WO | 2004054656 A1 | 7/2004 |
| WO | 2004078259 A1 | 9/2004 |
| WO | 2006050235 A1 | 5/2006 |
| WO | 2006050325 A2 | 5/2006 |
| WO | 2007077997 A1 | 7/2007 |
| WO | 2010025432 A1 | 3/2010 |
| WO | 2010077997 A2 | 7/2010 |

OTHER PUBLICATIONS

O'Keeffe et al., "Reproducability and responsiveness of quality of life assessment and six minute walk test in elderly heart failure patients," Heart (1998) 80: 377-382.

Office Action from corresponding Chinese Patent Application Serial No. 201180035326.2 dated Apr. 23, 2014.

Extended Search Report from corresponding European Application No. 11784088.4, dated Oct. 23, 2014.

* cited by examiner

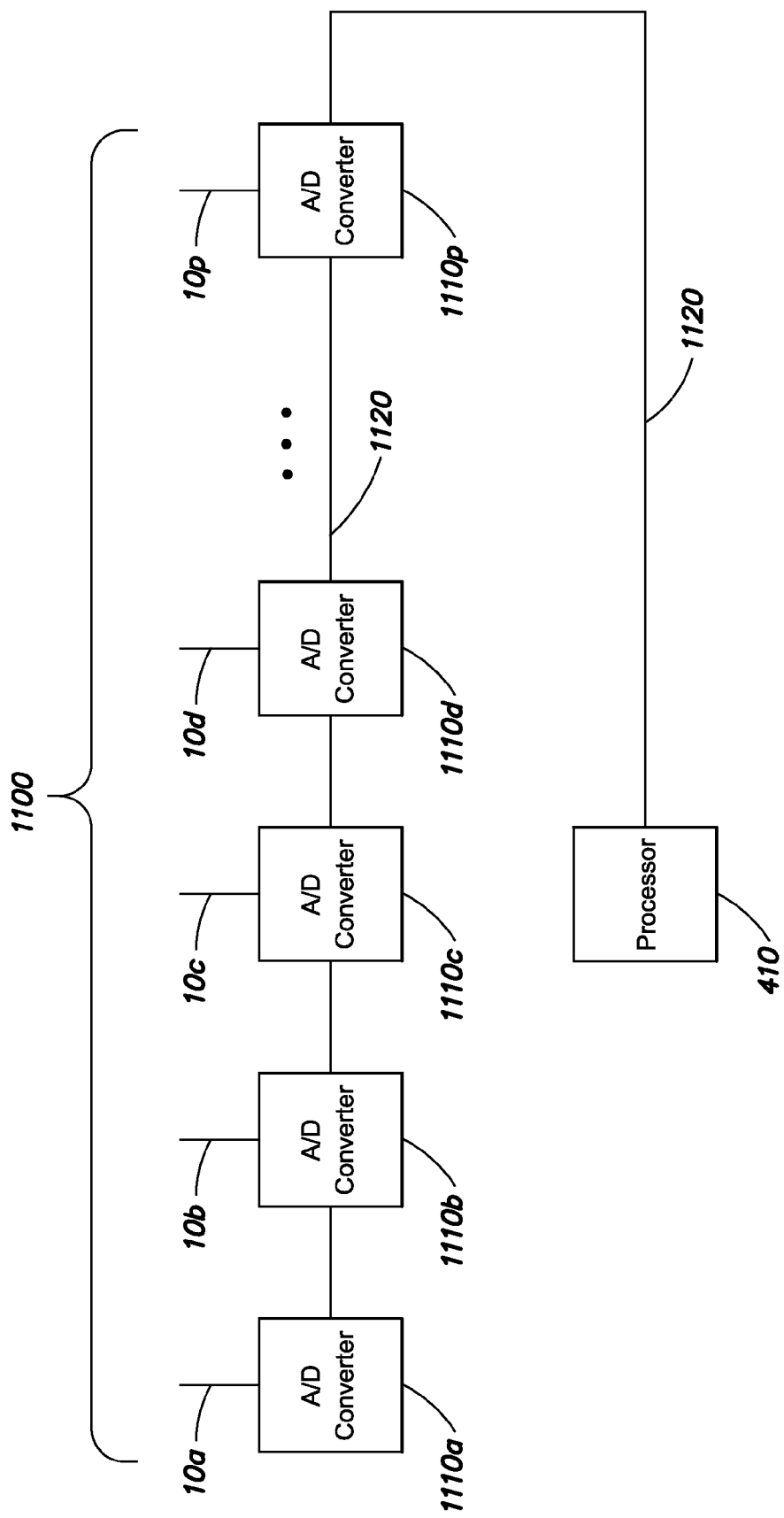

WEARABLE AMBULATORY MEDICAL DEVICE WITH MULTIPLE SENSING ELECTRODES

CROSS REFERENCE TO RELATED APPLICATIONS

This application is a Continuation of U.S. patent application Ser. No. 13/109,382 (now U.S. Pat. No. 8,706,215), titled "WEARABLE AMBULATORY MEDICAL DEVICE WITH MULTIPLE SENSING ELECTRODES," filed May 17, 2011 which is incorporated herein by reference in its entirety. U.S. patent application Ser. No. 13/109,382 claims priority under 35 U.S.C. §119(e) to U.S. Provisional Application Ser. No. 61/345,914 titled "WEARABLE AMBULATORY MEDICAL DEVICE WITH MULTIPLE SENSING ELECTRODES," filed May 18, 2010, and to U.S. Provisional Application Ser. No. 61/424,344 titled "WEARABLE AMBULATORY MEDICAL DEVICE WITH MULTIPLE SENSING ELECTRODES," filed Dec. 17, 2010, each of which is incorporated herein by reference in its entirety.

BACKGROUND OF INVENTION

1. Field of Invention

The present invention is generally directed to the detection of cardiac function in a patient, and more particularly to the detection of cardiac function and the treatment of cardiac conditions in an ambulatory medical device, such as a wearable defibrillator.

2. Discussion of Related Art

With a portable medical device, such as a wearable defibrillator worn by an ambulatory patient, the patient's electrocardiogram (ECG) signal is obtained from body surface electrodes. When the ECG signal is obtained in this manner, electrical noise or electrode fall-off frequently degrades the quality of the ECG signal. The challenge becomes one of extracting a clean ECG signal from the sometimes noisy signals derived from the body-surface electrodes.

Electrode noise can be caused by electrodes sliding on the patient's body due to extreme patient movement, such as vigorous exercise. Noise can also be caused by a poorly fit electrode belt or garment allowing the electrodes to slide on the patient's body with minor patient movement. Electrode fall-off can be caused by the electrodes flipping over and losing contact with the body, or lifting from the body and losing contact. Even where the electrodes are properly positioned on the patient's body, excessively dry skin can also cause noise.

Known ambulatory wearable defibrillators, such as the LifeVest® Wearable Cardioverter Defibrillator available from Zoll Medical Corporation of Chelmsford, Mass., use four ECG sensing electrodes in a dual-channel configuration. That is, an electrical signal provided by one of the four ECG sensing electrodes is paired with the electrical signal provided by another of the four ECG sensing electrodes to form a channel. This arrangement of ECG sensing electrodes is usually suitable because in most cases it is rare that noise or electrode movement affects the entire body circumference. The dual-channel configuration provides redundancy and allows the system to operate on a single channel if necessary, when one of the channels is declared unusable due to ECG sensing electrode fall-off, or to an inferior signal-to-noise ratio. Because signal quality also varies from patient to patient, having two channels provides the opportunity to have improved signal pickup, since the ECG sensing electrodes are located in different body positions. The two channel system also allows analysis of the ECG signal to determine cardiac conditions as described in U.S. Pat. No. 5,944,669.

A problem with existing electrode systems used in ambulatory medical treatment devices, such as a wearable defibrillator, is that there are still instances where there is noise on both channels. When there is noise or fall-off, the device issues alarms so that the patient can take action to correct the problem. With a noisy ECG signal, the arrhythmia detection algorithm in the wearable defibrillator device can be "fooled" into detecting the noise as an arrhythmia, thereby causing the device to issue a treatment sequence that, if not terminated by the patient, could deliver an unnecessary shock.

SUMMARY OF INVENTION

Embodiments of the present invention are directed to a wearable medical monitoring device and/or to a wearable medical monitoring and treatment device that incorporates multiple ECG sensing electrodes disposed at different axial positions around the body of a patient and that can choose from multiple channels corresponding to different pairings of those multiple ECG sensing electrodes to vastly improve the quality of the ECG signal obtained. This improved ECG sensor design can be used to reduce noise, to reduce the number of fall-off alarms, to reduce the number of cardiac arrhythmia false detections, or all of the above. The multiple channels provide different views of the heart's electrical activity and can be used to improve the detection sensitivity and specificity.

In accordance with one aspect of the present invention, an ambulatory medical device is provided. In one embodiment, the ambulatory medical device comprises a plurality of electrodes configured to be disposed at spaced apart positions about a body of a patient, an electrode signal acquisition circuit, and a monitoring circuit. The electrode signal acquisition circuit has a plurality of inputs, each respective input of the plurality of inputs being electrically coupled to a respective electrode of the plurality of electrodes. The electrode signal acquisition circuit is configured to sense a respective signal provided by a plurality of different pairings of the plurality of electrodes. The monitoring circuit is electrically coupled to an output of the electrode signal acquisition circuit. The monitoring circuit is configured to analyze the respective signal provided by each of the plurality of different pairings and to instruct the electrode signal acquisition circuit to select at least one of the plurality of different pairings to monitor based upon at least one of a quality of the respective signal provided by the selected at least one of the plurality of different pairings, a phase difference between the respective signal provided by the selected at least one of the plurality of different pairings and the respective signal provided by another selected at least one of the plurality of different pairings, a position of the respective electrodes of the selected at least one of the plurality of different pairings relative to the body of the patient, a plane defined by the respective electrodes of the selected at least one of the plurality of different pairings, and a cardiac cycle of a heart of the patient.

In accordance with one embodiment, the ambulatory medical device further comprises a garment that is configured to be worn about the body of the patient, and the plurality of electrodes are integrated into the garment. In accordance with another embodiment, the plurality of electrodes are ECG sensing electrodes, and the monitoring circuit is a cardiac monitoring and arrhythmia detection circuit.

In one embodiment, the plurality of ECG sensing electrodes includes at least three ECG sensing electrodes. In another embodiment, the plurality of ECG sensing electrodes are not all located in a common plane.

In one embodiment, the cardiac monitoring and arrhythmia detection circuit is configured to analyze the respective signal provided by each of the plurality of different pairings and to instruct the electrode signal acquisition circuit to select the at least one of the plurality of different pairings to monitor based upon the quality of the respective signal provided by the selected at least one of the plurality of different pairings and the phase difference between the respective signal provided by the selected at least one of the plurality of different pairings and the respective signal provided by the other selected at least one of the plurality of different pairings. In accordance with a further aspect of this embodiment, the ambulatory medical device further comprises a plurality of therapy electrodes integrated into the garment and configured to deliver a defibrillating shock to the body of the patient in response to detection of a treatable cardiac arrhythmia by the cardiac monitoring and arrhythmia detection circuit.

In accordance with another embodiment, the cardiac monitoring and arrhythmia detection circuit is configured to analyze the respective signal provided by each of the plurality of different pairings and to instruct the electrode signal acquisition circuit to select the at least one of the plurality of different pairings to monitor based upon the quality of the respective signal provided by the selected at least one of the plurality of different pairings and the plane defined by the respective electrodes of the selected at least one of the plurality of different pairings.

In another embodiment, the cardiac monitoring and arrhythmia detection circuit is configured to analyze the respective signal provided by each of the plurality of different pairings and to instruct the electrode signal acquisition circuit to select the at least one of the plurality of different pairings to monitor based upon the position of the respective electrodes of the selected at least one of the plurality of different pairings relative to the body of the patient and the cardiac cycle of the heart of the patient.

In an alternative embodiment, the cardiac monitoring and arrhythmia detection circuit is configured to select at least three of the plurality of different pairings to monitor based upon the at least one of the quality of the respective signal provided by each of the selected at least three of the plurality of different pairings, the phase difference between the respective signal provided by each of the selected at least three of the plurality of different pairings, the position of the respective electrodes of the selected at three of the plurality of different pairings relative to the body of the patient, the plane defined by the respective electrodes of the selected at least three of the plurality of different pairings, and the cardiac cycle of the heart of the patient.

In one embodiment, the plurality of electrodes includes at least four ECG sensing electrode that are not all located in a common plane.

In accordance with one embodiment, the monitoring circuit is configured to analyze the respective signal provided by each of the plurality of different pairings and to instruct the electrode signal acquisition circuit to select the at least one of the plurality different pairings to monitor based upon the quality of the respective signal provided by the selected at least one of the plurality of different pairings and the phase difference between the respective signal provided by the selected at least one of the plurality of different pairings and the respective signal provided by the other selected at least one of the plurality of different pairings.

In accordance with another embodiment, the monitoring circuit is configured to analyze the respective signal provided by each of the plurality of different pairings and to instruct the electrode signal acquisition circuit to select the at least one of the plurality of different pairings to monitor based upon the quality of the respective signal provided by the selected at least one of the plurality of different pairings and the plane defined by the respective electrodes of the selected at least one of the plurality of different pairings.

In accordance with yet another embodiment, the monitoring circuit is configured to analyze the respective signal provided by each of the plurality of different pairings and to instruct the electrode signal acquisition circuit to select the at least one of the plurality of different pairings to monitor based upon the position of the respective electrodes of the selected at least one of the plurality of different pairings relative to the body of the patient and the cardiac cycle of the heart of the patient.

In accordance with one embodiment, the monitoring circuit is configured to select at least three of the plurality of different pairings to monitor based upon the at least one of the quality of the respective signal provided by each of the selected at least three of the plurality of different pairings, the phase difference between the respective signal provided by each of the selected at least three of the plurality of different pairings, the position of the respective electrodes of the selected at three of the plurality of different pairings relative to the body of the patient, the plane defined by the respective electrodes of the selected at least three of the plurality of different pairings, and the cardiac cycle of the heart of the patient. In accordance with a further embodiment, the monitoring circuit is configured to select at least two of the selected at least three of the plurality of different pairings to monitor during a first time interval and to select a different at least two of the selected at least three of the plurality of different pairings to monitor during a second time interval.

In one embodiment, the plurality of ECG sensing electrodes includes at least three ECG sensing electrodes.

In accordance with one embodiment, the electrode signal acquisition circuit includes a selection circuit and a plurality of differential amplifiers. The selection circuit has a plurality of inputs and a plurality of outputs, each respective input of the plurality of inputs of the selection circuit being electrically coupled to a respective one of the plurality of electrodes. Each respective differential amplifier of the plurality of differential amplifiers has a pair of inputs and an output, each respective input of the pair of inputs being electrically coupled to a respective one of the plurality of outputs of the selection circuit, each respective output of the plurality of differential amplifiers providing an output signal corresponding to a difference between the pair of inputs of the respective differential amplifier.

In accordance with another embodiment in which the electrode signal acquisition circuit includes a plurality of differential amplifiers and a selection circuit, the plurality of differential amplifiers includes a respective differential amplifier for each unique pairing of the plurality of electrodes. In this embodiment, the selection circuit is configured to select at least one output of the plurality of differential amplifiers to provide to the monitoring circuit.

In accordance with another embodiment, the electrode signal acquisition circuit includes an analog multiplexer and an analog-to-digital converter. The analog multiplexor has a plurality of inputs and an output, each of the plurality of inputs being electrically coupled to a respective one of the plurality of electrodes, and the analog-to-digital converter has an input electrically coupled to the output of the analog multiplexer. In accordance with an aspect of this embodiment, the analog-to digital converter has a sampling rate that is at least N times a desired sampling rate of a signal provided by each of the plurality of electrodes, where N is the number of the plurality of electrodes that are to be monitored. In accordance with another aspect of this embodiment, the monitoring circuit includes at least one processor configured to receive a first digital signal corresponding to a first electrode of the plurality of electrodes and a second digital signal corresponding to a second electrode of the plurality of electrodes, to invert one of the first and second digital signals and sum the inverted one of the first and second digital signals with the other of the first and second digital signals to analyze the respective signal provided by a pairing of the first electrode and the second electrode.

In accordance with another embodiment, the electrode signal acquisition circuit includes a plurality of analog-to-digital converters, each respective analog-to-digital converter having a respective input that is electrically coupled to a respective one of the plurality of electrodes. In one embodiment, each of the plurality of analog-to-digital converters is connected to another of the plurality of analog-to-digital converters by a serial bus.

In accordance with another aspect of the present invention, a method of monitoring ECG signals is provided. In one embodiment, the method comprises selecting, from among a plurality of ECG sensors, a plurality of different pairings of ECG sensors; analyzing a respective ECG signal provided by each of the plurality of different pairings; identifying at least one of the plurality of different pairings to monitor based upon at least one of a quality of the respective ECG signal provided by the identified at least one of the plurality of different pairings, a phase difference between the respective ECG signal provided by the identified at least one of the plurality of different pairings and the respective ECG signal provided by another identified at least one of the plurality of different pairings, a position of respective ECG sensors of the identified at least one of the plurality of different pairings relative to a body of a patient, a plane defined by the respective ECG sensors of the identified at least one of the plurality of different pairings, and a cardiac cycle of a heart of the patient; and monitoring the identified at least one of the plurality of different pairings.

In accordance with one embodiment, the act of identifying at least one of the plurality of different pairings to monitor is based upon the quality of the respective ECG signal provided by the identified at least one of the plurality of different pairings and the phase difference between the respective ECG signal provided by the identified at least one of the plurality of different pairings and the respective ECG signal provided by the other identified at least one of the plurality of different pairings.

In one embodiment, the act of selecting the plurality of different pairings of ECG sensors from among the plurality of ECG sensors includes an act of selecting, from among the plurality of ECG sensors, each unique pairing of ECG sensors, and the act of analyzing the respective ECG signal provided by each of the plurality of different pairings includes analyzing the respective ECG signal provided by each unique pairing of ECG sensors.

In a further embodiment, the act of monitoring includes monitoring the identified at least one of the plurality of different pairings to detect a cardiac arrhythmia. In accordance with one embodiment, the method further comprises acts of detecting the cardiac arrhythmia responsive to the act of monitoring; determining that the detected cardiac arrhythmia is a type of cardiac arrhythmia that can be treated by applying defibrillation to the body of the patient; and applying at least one defibrillation pulse to the body of the patient.

In another embodiment, the method further comprises acts of detecting the cardiac arrhythmia responsive to the act of monitoring; selecting at least one additional pairing of ECG sensors in response to detecting the cardiac arrhythmia and analyzing the respective ECG signal provided by the at least one additional pairing; determining that the detected cardiac arrhythmia is also present on the respective ECG signal of the at least one additional pairing; determining that the detected cardiac arrhythmia is a type of cardiac arrhythmia that can be treated by applying defibrillation to the body of the patient; and applying at least one defibrillation pulse to the body of the patient.

In an alternative embodiment, the method further comprises acts of detecting the cardiac arrhythmia responsive to the act of monitoring; selecting at least one additional pairing of ECG sensors in response to detecting the cardiac arrhythmia and analyzing the respective ECG signal provided by the at least one additional pairing; determining that the detected cardiac arrhythmia is also present on the respective ECG signal of the at least one additional pairing; and increasing a confidence level that the cardiac arrhythmia has been detected.

In another embodiment, the method further comprises acts of detecting the cardiac arrhythmia responsive to the act of monitoring; selecting at least one additional pairing of ECG sensors in response to detecting the cardiac arrhythmia and analyzing the respective ECG signal provided by the at least one additional pairing; determining that the detected cardiac arrhythmia is not present on the respective ECG signal of the at least one additional pairing; and decreasing a confidence level that the cardiac arrhythmia has been detected.

In accordance with one embodiment, the acts of selecting, analyzing, and identifying are repeated at periodic intervals.

In accordance with another embodiment, the plurality of ECG sensors are integrated in a garment that is worn about the body of the patient, and the acts of selecting, analyzing, and identifying are performed each time the garment is placed about the body of the patient.

In accordance with another embodiment in which the plurality of ECG sensors are integrated in a garment that is worn about the body of the patient, the method further comprises an act of detecting strenuous physical activity of the patient, and repeating the acts of selecting, analyzing, and identifying in response to the act of detecting the strenuous activity of the patient.

In accordance with another embodiment, the method further comprises acts of determining that the quality of the respective ECG signal provided by a first pairing of ECG sensors of the identified at least one of the plurality of different pairings is below a determined threshold; selecting another paring of ECG sensors to replace the first pairing of ECG sensors; and monitoring the other pairing of ECG sensors.

In accordance with yet another embodiment, the method further comprises acts of determining, from the quality of the respective ECG signal provided by a first pairing of ECG sensors of the identified at least one of the plurality of different pairings, that one or more of the ECG sensors of the first pairing may have at least partially lost contact with the body of the patient; selecting another paring of ECG sensors to replace the first pairing of ECG sensors; and monitoring the other pairing of ECG sensors.

In accordance with one embodiment, the act of identifying at least one of the plurality of different pairings to monitor is based upon the quality of the respective ECG signal provided by the identified at least one of the plurality of different pairings and the plane defined by the respective ECG sensors of the identified at least one of the plurality of different pairings.

In accordance with another embodiment, the act of identifying at least one of the plurality of different pairings to monitor is based upon the position of respective ECG sensors of the identified at least one of the plurality of different pairings relative to the body of the patient and the cardiac cycle of the heart of the patient.

Still other aspects, embodiments, and advantages of these exemplary aspects and embodiments, are discussed in detail below. Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with at least one aspect of the invention disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment. Furthermore, in the event of inconsistent usages of terms between this document and documents incorporate herein by reference, the term usage in the incorporated references is supplementary to that of this document; for irreconcilable inconsistencies, the term usage in this document controls.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 11 illustrates another alternative signal acquisition circuit that may be used with embodiments of the present invention.

DETAILED DESCRIPTION

Figure 1A:
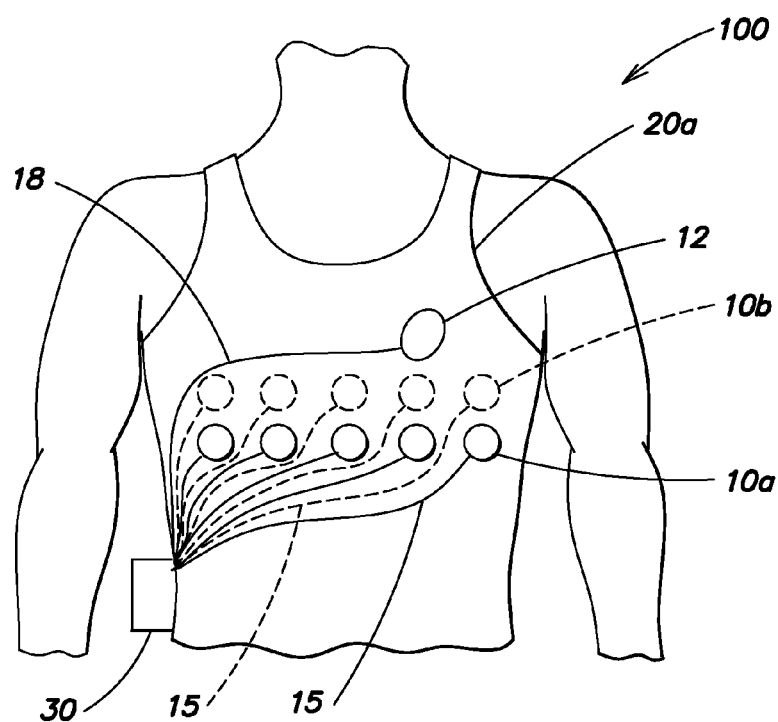
FIG. 1A illustrates an electrode system of a portable medical device in which a plurality of ECG sensing electrodes are integrated into a garment, such as a shirt or vest that can be worn on the body of the patient, and in which the electrodes are generally disposed in a plane of the patient's heart.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

U.S. Pat. No. 5,944,669, which is incorporated herein by reference in its entirety, describes a method and apparatus for sensing cardiac function in a patient that may be used to initiate treatment of a detected cardiac condition. ECG sensing electrodes are used to obtain ECG signals from the heart of the patient and those ECG signals are analyzed using various techniques to provide information indicative of the operation of the patient's heart, and whether a treatable cardiac condition is present for which treatment, such as defibrillation, should be initiated. As described therein, a plurality of pairs of ECG sensing electrodes are used, such that signals received from the different pairs of ECG sensing electrodes may be compared to one another to improve reliability or detection, so that noise present on one or more of the electrodes can be identified, so that monitoring may be provided even in the event that one or more of the sensing electrodes falls off, etc.

Embodiments of the present invention are directed to an electrode system that may be used in a wearable medical device, such as that described in U.S. Pat. No. 5,944,669 (hereinafter "the '669 patent"), to monitor cardiac function, to initiate treatment of a detected cardiac condition, or both. As described in more detail below, although embodiments of the present invention are primarily described in terms of monitoring signals from a plurality of ECG sensing electrodes, it should be appreciated that the techniques described herein may readily be extended for use with other types of sensors, other than ECG sensing electrodes. For example, other types of sensors may include activity sensors, such as multiple axis accelerometers, pulse oxygen sensors, temperature sensors, respiratory rate sensors, thoracic impedance sensors, blood pressure sensors, acoustic sensors, etc.

As shown in FIG. 1A, in one embodiment of the present invention, the electrode system 100 includes a plurality of ECG sensing electrodes 10 that are disposed at different axial positions around the body of a patient and integrated into a garment 20a, such as a shirt or vest which is worn on the torso of the patient. As depicted in FIG. 1A (as well as in FIGS. 1B-1F), those ECG electrodes shown in solid line form are disposed on the front of the patient's body, while those ECG electrodes shown in dotted line form are disposed on the back of the patient's body. It should be appreciated that although not depicted in the figures, the plurality of ECG sensing electrodes 10 will generally include electrodes disposed on the sides of the patient's body, as well as electrodes disposed on the front and back of the patient's body.

The plurality of ECG sensing electrodes 10 may be discrete, dry-sensing capacitive or conductive electrodes that are, for example, attached to the garment 20a by an adhesive or hook and loop fastener, magnetically attached to the garment 20a, or alternatively, sewn into the garment 20a. Alternatively still, some or all of the ECG sensing electrodes may be formed from electrically conductive threads sewn into the garment 20a, such as described in U.S. patent application Ser. No. 13/109,079, titled "WEARABLE THERAPEUTIC DEVICE," filed on May 17, 2011 (now U.S. Pat. No. 9,008, 801), which is incorporated herein by reference in its entirety. It should be appreciated that the present invention is not limited to a particular type of ECG sensing electrode or method of attachment, as various types of ECG sensing electrodes, including wet ECG sensing electrodes, and various methods of attachment, including adhesive attachment to the patient's body may be used. Moreover, although embodiments of the present invention are primarily described with respect to ECG sensing electrodes that are electrically coupled to a control unit by wires, the present invention is not so limited, as embodiments of the present invention may also be used with ECG sensing electrodes that communicate with a control unit using a wireless communication interface and protocol, such as Bluetooth, Wireless USB, ZigBee, Wireless Ethernet, GSM, etc. as discussed further below.

As shown in FIG. 1A, the plurality of ECG sensing electrodes 10 are deployed about the body of the patient at spaced apart axial positions generally located in a plane of the heart of the patient. In accordance with one embodiment of the present invention, the ECG sensing electrodes 10 are deployed about the body of the patient in pairs of generally opposed electrodes (e.g., ECG sensing electrodes 10a, 10b) that are integrated into a garment 20a, such as a shirt or vest, although the present invention is not so limited. It should be appreciated that the location of the plurality of ECG sensing electrodes 10 may be varied to avoid placing an electrode in a location where it could promote discomfort for the patient, such as directly on the spine of the patient. Insulated lead wires 15 electrically couple each ECG sensing electrode of the plurality of ECG sensing electrodes 10 to a control unit 30 that may include a signal acquisition circuit, such as that described in more detail with respect to FIGS. 2A-C, 3, 9, 10, and 11 below. Although not shown, each of the insulated lead wires 15 may be electrically connected to a connector that is received in a receptacle of the control unit 30. The control unit 30 may be attached to the garment 20a, attached to a belt, received in a holster, or attached to a clip so that it may be easily worn by the patient, or the control unit 30 may be carried with the patient in any other convenient manner. As shown, the electrode system 100 also includes at least one driven ground electrode 12 that is attached to the garment 20a and is electrically coupled to the control unit 30 by an insulated lead wire 18. The at least one driven ground electrode 12 may be used in the manner described in the '669 patent to reduce the effects of noise and/or detect if an ECG sensing electrode has fallen off. Although the use of a driven ground electrode is preferred to cancel the effects of noise, it should be appreciated that the electrode 12 need not be actively driven, and could simply be a passive circuit ground.

Figure 1B:
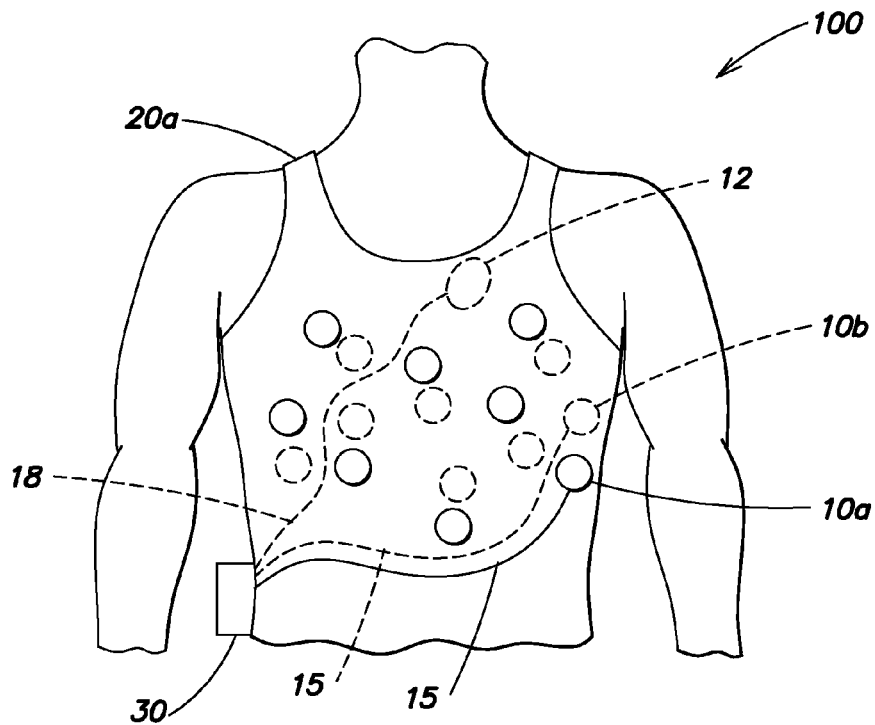
FIG. 1B illustrates an alternative electrode system of a portable medical device in which the plurality of ECG sensing electrodes are integrated into a garment such as that depicted in FIG. 1A, but in which the electrodes are distributed about the torso of the patient.

FIG. 1B illustrates an electrode system 100 in accordance with an alternative embodiment of the present invention in which the plurality of ECG sensing electrodes 10 are again integrated into a garment 20a, such as a shirt or vest that is worn over the torso of a patient. However, in the embodiment depicted in FIG. 1B, the plurality of ECG sensing electrodes 10 are distributed about the torso of the patient, rather than being generally located in a plane of the patient's heart. As in the embodiment of FIG. 1A, the plurality of ECG sensing electrodes 10 are electrically coupled to a control unit 30 by a respective electrically insulated lead wire 15 (not all of which are shown for ease of illustration), although wireless ECG sensing electrodes could alternatively be used. The electrode system 100 also includes at least one driven ground electrode 12 that is attached to the garment 20a and electrically coupled to the control unit by an insulated lead wire 18. Although only one driven ground electrode 12 is illustrated in the figures, it should be appreciated that multiple driven ground electrodes may be used. For example, multiple driven ground electrodes may be provided, with one of the driven ground electrodes being used with certain pairings of ECG sensing electrodes, and another of the driven ground electrodes being used with other pairings of ECG sensing electrodes. Moreover in certain embodiments, the at least one driven ground electrode may be switched to be used with different pairings of ECG sensing electrodes. For example, if it were determined that one of the driven ground electrodes had fallen off or had poor contact with the body of the patient, another of the driven ground electrodes could be used instead.

The plurality of ECG sensing electrodes 10 may be deployed in pairs (e.g., ECG electrodes 10a, 10b) of generally opposed electrodes, or simply spaced apart about the torso of the patient. Although not shown in FIG. 1B, the plurality of ECG sensing electrodes 10 may include a first grouping of electrodes that are located at spaced apart axial positions generally located in the plane of the patient's heart, and a second grouping of electrodes that are located at varying position about the torso of the patient. As discussed in more detail further below, the presence of ECG sensing electrodes that are not all co-located in the plane of the patient's heart permits the selection of different pairings of ECG sensing electrodes that can correspond to different planes intersecting the patient's heart. Moreover, although not depicted in FIG. 1B, the plurality of ECG sensing electrodes 10 may include ECG sensing electrodes positioned on side of the patient's torso, as well as the patient's front and back. As the embodiment of FIG. 1B is substantially similar to that of FIG. 1A, further discussion of those elements common to both embodiments is omitted herein.

Figure 1C:
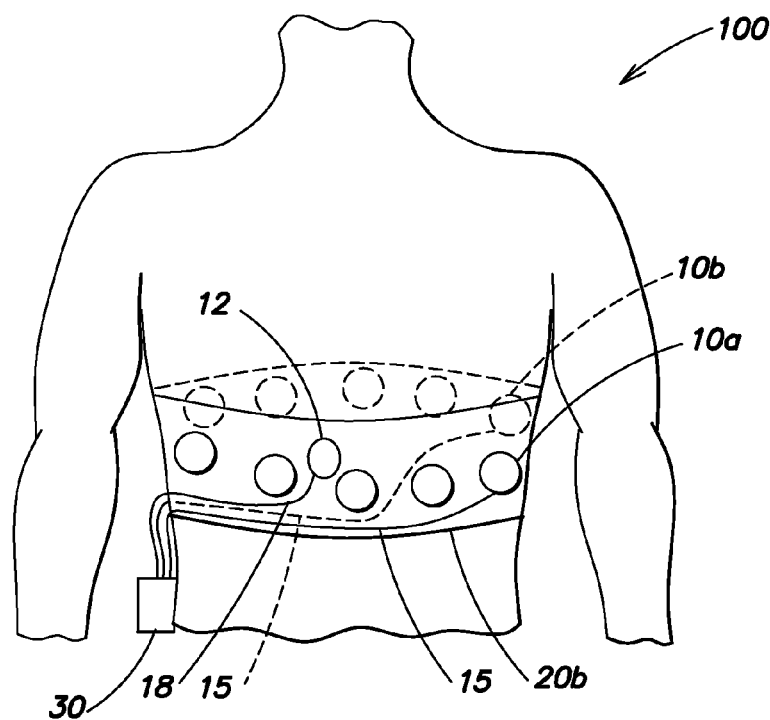
FIG. 1C illustrates an alternative electrode system of a portable medical device in which the plurality of ECG sensing electrodes are integrated into a garment, such as a belt that can be worn on the body of the patient, and in which the electrodes are generally disposed in a plane of the patient's heart.

FIG. 1C illustrates an electrode system 100 in accordance with a further embodiment of the present invention in which the plurality of ECG sensing electrodes 10 are again disposed at different axial positions around the body of a patient and generally located in a plane of the heart of the patient as in FIG. 1A. However, in the embodiment depicted in FIG. 1C, the plurality of ECG sensing electrodes 10 are integrated into a garment 20b, such as a belt, that is worn about the torso of the patient. As with the electrode system of FIGS. 1A and 1B, the electrode system 100 of FIG. 1C may include any type of ECG sensing electrodes, such as discrete, dry-sensing capacitive or conductive electrodes that are attached to the garment 20b by an adhesive or fastener, magnetically attached to the garment 20b, or sewn into the garment 20b. As with the embodiment of FIGS. 1A and 1B, the plurality of ECG sensing electrodes 10 may be deployed about the patient's body in pairs of generally opposed electrodes (e.g., ECG sensing electrodes 10a, 10b), or may simply be axially spaced about the torso of the patient. Lead wires 15 (not all of which are shown for ease of illustration) electrically couple each ECG sensing electrode of the plurality of ECG sensing electrodes 10 to the control unit 30, which may be worn on or carried with the body of the patient. It should be appreciated that wireless ECG sensing electrodes could alternatively be used. As in the embodiments described previously with respect to FIGS. 1A and 1B, the electrode system 100 of FIG. 1C also includes at least one driven ground electrode 12 that is attached to the garment 20b and may be used to reduce the effects of noise and/or detect if an ECG sensing electrode has fallen off. The at least one driven ground electrode 12 may be disposed in the same plane as the plurality of ECG sensing electrodes 10, or may be located in a different plane. In some embodiments, the at least one driven ground electrode 12 may also be used as a therapy electrode to administer an electrical shock to the heart of the patient, as discussed further with respect to FIG. 1E below. Although not depicted in FIG. 1C, the plurality of ECG sensing electrodes 10 may include ECG sensing electrodes positioned on side of the patient's torso, as well as the patient's front and back.

Figure 1D:
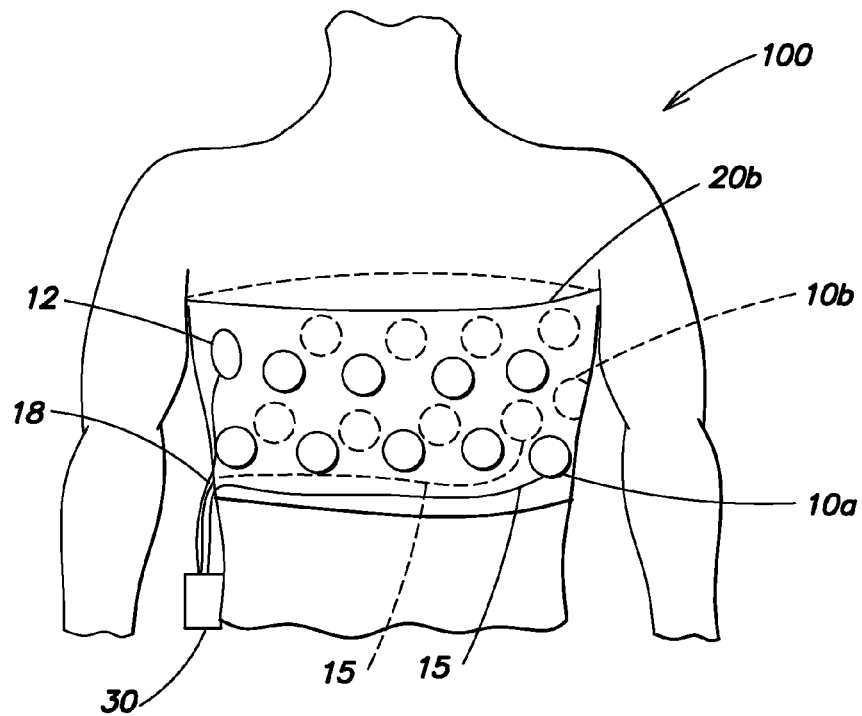
FIG. 1D illustrates an alternative electrode system of a portable medical device in which the plurality of ECG sensing electrodes are integrated into a garment, such as a belt that can be worn on the body of the patient, and in which the electrodes are distributed about a portion of the torso of the patient.

FIG. 1D illustrates an electrode system 100 in accordance with yet another embodiment of the present invention in which the plurality of ECG sensing electrodes 10 are again integrated into a garment 20b, such as a belt that is worn over the torso of a patient, but in which the plurality of ECG sensing electrodes 10 are distributed more widely about the torso of the patient. As in the embodiment of FIGS. 1A-C, the plurality of ECG sensing electrodes 10 are electrically coupled to a control unit 30 by a respective electrically insulated lead wire 15 (not all of which are shown for ease of illustration), and the electrode system 100 also includes at least one driven ground electrode 12. The at least one driven ground electrode 12 may include a first driven ground electrode that is generally disposed in a same plane as a plurality of the ECG sensing electrodes, and a second driven ground electrode disposed in a different plane. The plurality of ECG sensing electrodes 10 may be deployed in pairs (e.g., ECG electrodes 10a, 10b), or simply spaced apart about the torso of the patient. As the embodiment of FIG. 1D is substantially similar to that of FIGS. 1A-C, further discussion of those elements that are in common with FIGS. 1A-C is omitted herein.

Figure 1E:
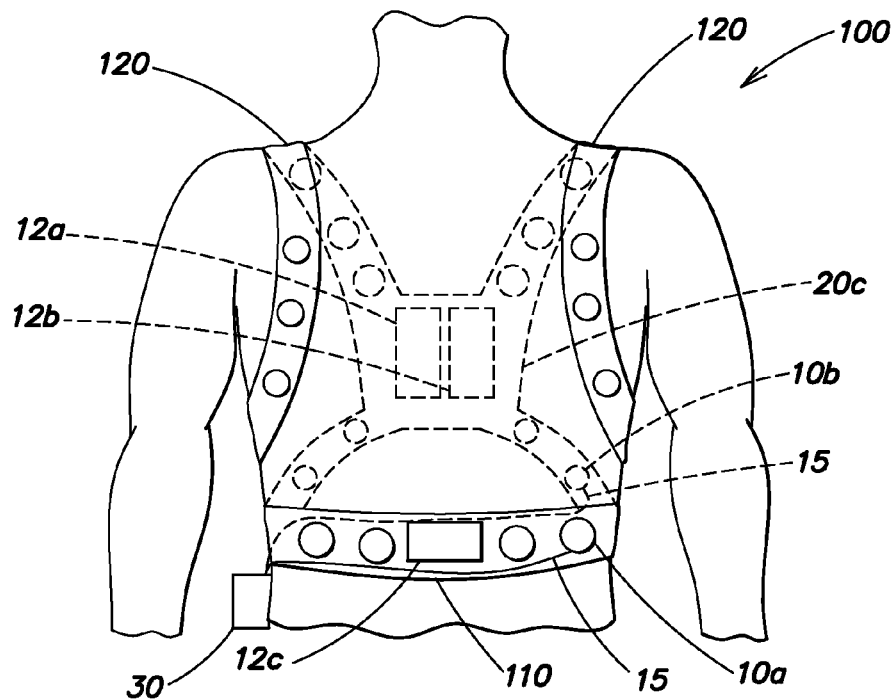
FIG. 1E illustrates a further alternative electrode system of a portable medical device in which the plurality of ECG sensing electrodes are integrated into a garment, such as a harness, and in which the electrodes are disposed about the torso of the patient.

FIG. 1E illustrates an electrode system 100 in accordance with an alternative embodiment of the present invention in which the plurality of ECG sensing electrodes 10 are again integrated into a garment 20c. However, in this embodiment, the garment 20c is constructed in the form of a harness, such as that used in the LifeVest® Wearable Cardioverter Defibrillator. The harness includes an adjustable belt 110 and adjustable shoulder straps 120 that permit the harness be easily adjusted to fit different body types and sizes.

As shown in FIG. 1E, the plurality of ECG sensing electrodes 10 are disposed about the body of the patient at varying locations along the belt 110 and shoulder straps 120 of the garment 20c. As with the previously described embodiments, the plurality of ECG sensing electrodes 10 may be discrete, dry-sensing capacitive or conductive electrodes that are attached to the garment 20c, for example, by an adhesive, by hook and loop fasteners, or by sewing, or alternatively, the electrodes may be formed from electrically conductive threads sewn into the garment 20c. As with the previously described embodiments, the plurality of ECG sensing electrodes 10 may be deployed in pairs of generally opposed electrodes (e.g., ECG sensing electrodes 10a and 10b), or alternatively, may not be deployed in pairs, but simply disposed at various locations about the body of the patient. Although not depicted in FIG. 1E, the plurality of ECG sensing electrodes 10 will generally include ECG sensing electrodes disposed on the sides of the patient's body, as well as on the front and back of the patient's body.

As with the embodiments of FIGS. 1A-D, the electrode system 100 of FIG. 1E may include a control unit 30 that is electrically coupled to each of the plurality of ECG sensing electrodes 10 by a respective insulated lead wire 15, although wireless ECG sensing electrodes could alternatively be used. The control unit 30 may include a signal acquisition circuit, such as that described in more detail with respect to FIGS. 2A-C, 3, 9, 10, and 11, and the control unit may also include a controller that may not only monitor the ECG signals from the patient, but may analyze those ECG signals and initiate electrical shock therapy to the patient in the event that such treatment is warranted. The control unit 30 may be integrated into the garment 20c, attached to the belt 110, received in a holster (not shown), or attached to a clip so that it may be easily worn by the patient, or the control unit 30 may be carried with the patient in any other convenient manner.

As with the previously described embodiments, the electrode system 100 also includes at least one driven ground electrode 12. As illustrated in FIG. 1E, in at least one embodiment, the at least one driven ground electrode includes three driven ground electrodes 12a, 12b, and 12c. The driven ground electrodes 12a-c may be used in the manner described in the '669 patent to reduce the effects of noise and/or detect if an ECG sensing electrode has fallen off. In one embodiment of the present invention, the driven ground electrodes 12a-c can also be used as a therapy electrodes to deliver a defibrillating shock to the body of the patient, where such treatment is warranted. In this embodiment, the electrodes 12a and 12b are electrically coupled together and act as a first therapy electrode, with electrode 12c acting as a second therapy electrode. The use of two therapy electrodes permits a biphasic shock to be delivered to the body of the patient, such that a first of the two therapy electrodes delivers a first phase of the biphasic shock with the other therapy electrode acting as a return, and the other therapy electrode delivers the second phase of the biphasic shock with the first therapy electrode acting as the return. It should be appreciated that in some embodiments, a monophasic shock or other type of defibrillating pulse of energy may be used.

Figure 1F:
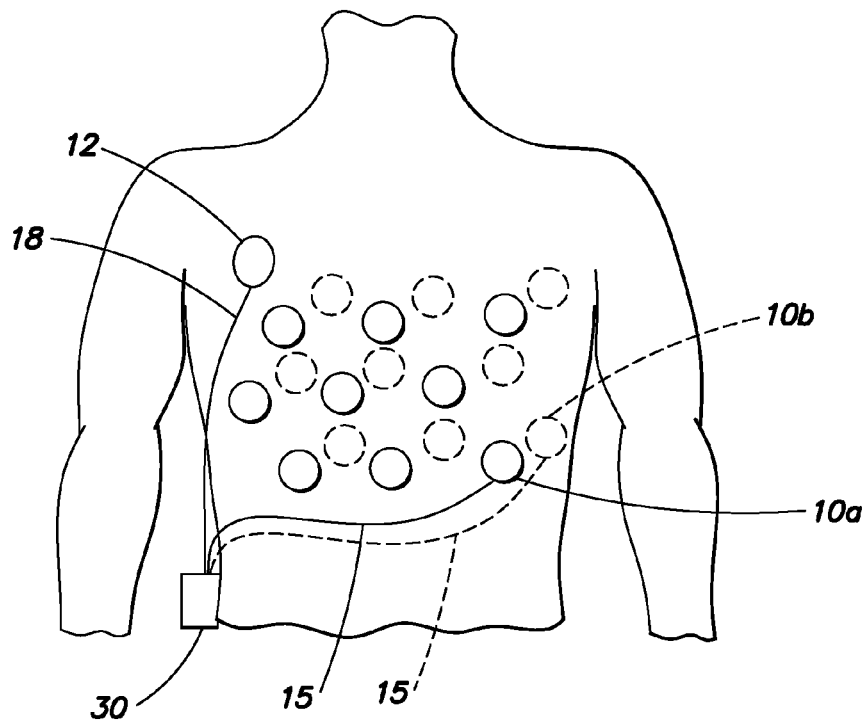
FIG. 1F illustrates an alternative electrode system of a portable medical device in which the plurality of ECG sensing electrodes are directly attached to the patient's torso.

FIG. 1F illustrates an electrode system 100 in accordance with another embodiment of the present invention that includes a plurality of ECG sensing electrodes 10. In contrast to the embodiments described with respect to FIGS. 1A-E, rather than being attached or integrated into a garment 20a, 20b, or 20c, each of the plurality of ECG sensing electrodes 10 and the at least one driven ground electrode 12 is directly attached to the body of the patient. As with the previously described embodiments, each of the plurality of ECG sensing electrodes 10 is electrically coupled to the control unit 30 by a respective insulating wire 15 (not all of which are shown for ease of illustration), and the electrode system 100 includes at least one driven ground electrode 12 that is electrically coupled to the control unit 30 by an insulated lead wire 18. In accordance with an aspect of the present invention, the control unit 30 may include a signal acquisition circuit that is capable of selecting, from among the plurality of ECG sensing electrodes 10, those pairs of electrodes that provide the best ECG signals, in terms of signal level, noise, phase discrimination, or any other criteria. As with the previously described embodiments of FIGS. 1A-E, the plurality of ECG sensing electrodes 10 may be deployed about the body of the patient in pairs of generally opposed electrodes (e.g., ECG sensing electrodes 10a, 10b), or simply spaced about the torso of the patient. Although not depicted in FIG. 1F, the plurality of ECG sensing electrodes 10 will typically include ECG sensing electrodes positioned on side of the patient's torso, as well as the patient's front and back. It should be appreciated that the embodiments of FIGS. 1A-E may additionally include one or more ECG sensing electrodes (or driven ground electrodes) that are directly attached to the body of the patient, in addition to those that are integrated into the garment 20a-20c.

Figure 1G:
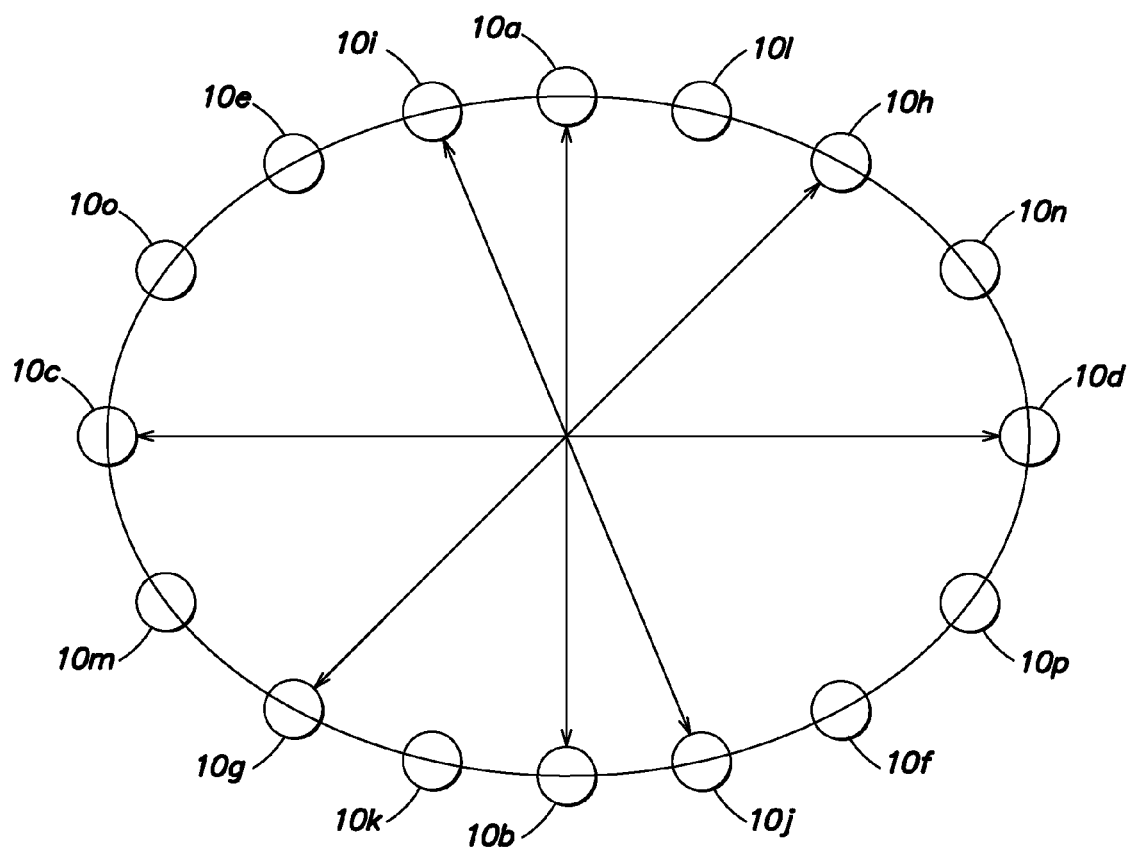
FIG. 1G illustrates a plan view of the electrode systems of FIGS. 1A-F.

FIG. 1G illustrates a plan view of electrode system 100 of FIGS. 1A-1E. As shown, the plurality of ECG sensing electrodes 10 are disposed at different axial positions about the body of the patient, although they need not be deployed in a single plane. Indeed, in at least one embodiment, the plurality of ECG sensing electrodes are not all co-located in a single plane so that pairs of electrodes corresponding to different planes may be selected. Further, although the plurality of ECG sensing electrodes 10 are shown as being deployed in generally diametrically opposed pairs of electrodes (e.g., electrodes 10a and 10b, electrodes 10c and 10d), it should be appreciated that the present invention is not so limited. In the embodiment depicted in FIG. 1G, the plurality of ECG sensing electrodes 10 includes 16 ECG sensing electrodes, with each ECG sensing electrode being spaced apart from an adjacent ECG sensing electrode by approximately 22.5°. In another embodiment, the plurality of ECG sensing electrodes 10 includes 12 sensing electrodes, with each ECG sensing electrode being spaced apart from an adjacent ECG sensing electrode by approximately 30°, and in a further embodiment, the plurality of ECG sensing electrodes includes 18 sensing electrodes spaced approximately 20° apart. It should be appreciated that more or fewer ECG sensing electrodes may be provided, for example, as few as three, and that some or all of the ECG sensing electrodes may be located outside of a horizontal plane intersecting the heart of the patient.

Advantageously, the use of multiple electrodes permits different pairings of ECG sensing electrodes to be selected, where that selection provides a better or more desirable ECG signal, in terms of signal level, noise immunity, phase difference, cardiac arrhythmia detection specificity, or any other criteria. For example, ECG sensing electrode 10a could be paired with either of ECG sensing electrodes 10k or 10j, rather than with ECG sensing electrode 10b, where such a pairing resulted in a better ECG signal level, better noise immunity, or a maximum phase discrimination, or where it was determined that ECG sensing electrode 10b had fallen off or has poor contact with the body of the patient. Different pairings of ECG sensing electrodes having a similar phase difference, or representing different phase differences may be selected and compared to one another. For example, ECG sensing electrodes 10g and 10h that are spaced approximately 180° apart may be paired and the ECG signal compared to that from ECG sensing electrodes 10c and 10d (also spaced 180° apart), or alternatively, ECG sensing electrodes 10g and 10h may be paired and the ECG signal compared to that from ECG sensing electrodes 10b and 10d that are spaced approximately 90° apart in order to screen out noise or derive additional information. Where the plurality of ECG sensing electrodes 10 are not all located in a single plane, the pairings of ECG sensing electrodes may be selected to correspond to different planes. It should be appreciated that the different pairings of ECG sensing electrodes need not be disjoint. For example, ECG sensing electrode 10a may be paired with ECG sensing electrode 10b and the ECG signal compared to that from ECG sensing electrodes 10a and 10c and/or to that from ECG sensing electrodes 10a and 10d.

Figure 2A:
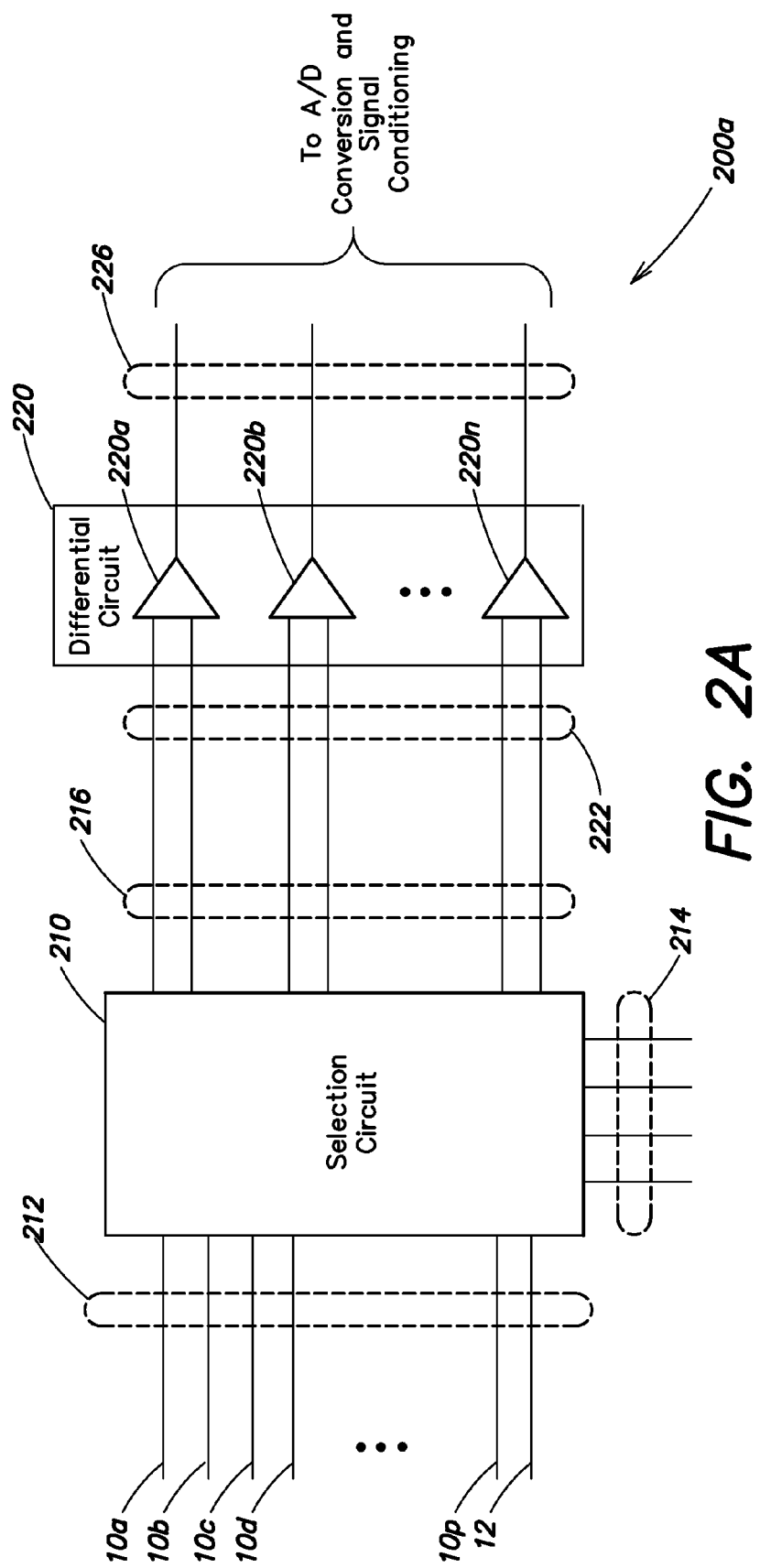
FIG. 2A illustrates an electrode signal acquisition circuit that may be used with embodiments of the present invention to select, from among a plurality of different pairings of ECG sensing electrodes, those pairings of electrodes that maximize the signal-to-noise ratio and maximize the phase discrimination provided by the electrodes.

FIG. 2A illustrates a signal acquisition circuit that may be used with embodiments of the present invention to select, from among a plurality of ECG sensing electrodes, those pairings of electrodes that provide a desired ECG signal, in terms of signal-to-noise ratio, phase discrimination, or any other criteria, and provide those ECG signals to downstream circuitry for further signal conditioning, processing, analysis, and/or monitoring. Advantageously, the signal acquisition circuit 200a depicted in FIG. 2A may be used as a front end to the analog to digital conversion and signal conditioning block 14 described with respect to the arrhythmia detection system of FIGS. 2a-2c of the '669 patent.

As shown, the signal acquisition circuit 200a includes a selection circuit 210 that is electrically coupled to a differential circuit 220. Signals from each of the plurality of ECG sensing electrodes 10a-10p are provided to a respective input 212 of the selection circuit 210. Signals from one or more of the driven ground electrodes 12 may also be provided to an input 212 of the selection circuit 210, such that a signal may be transmitted on the driven ground electrode 12, and that signal compared to the signals received on each of the plurality of ECG sensing electrodes to identify whether a particular ECG sensing electrode may have fallen off, or to identify noise issues relating to a particular ECG sensing electrode. The selection circuit 210 has a plurality of outputs 216 that are electrically coupled to respective inputs 222 of the differential circuit 220. In operation, the selection circuit 210 operates in a manner similar to a multiple output multiplexer, and includes a plurality of control inputs 214 to select signals from different ECG sensing electrodes and/or the driven ground electrode and provide those selected signals to the inputs 222 of the differential circuit 220. It should be appreciated that rather than a single selection circuit, a plurality of conventional single output multiplexers may be used to achieve the same functionality.

The differential circuit 220 includes a plurality of analog differential instrumentation amplifiers 220a, 220b, . . . 220n, to receive the signals provided by different pairings of the ECG sensing electrodes and/or different pairings of a respective ECG sensing electrode and a driven ground electrode and provide a respective differential output signal 226 corresponding to the difference therebetween. Where the signals provided to a respective amplifier 220a, 220b, . . . 220n correspond to signals provided by different ECG sensing electrodes, a differential ECG signal is provided. This differential analog ECG signal may then be digitally converted and conditioned by an analog-to-digital conversion and signal conditioning block of an arrhythmia detection system, such as that described with respect to FIGS. 2a-2c of the '669 patent, prior to further analysis and/or monitoring by an arrhythmia monitoring and/or treatment system, such as a wearable defibrillator.

Figure 2B:
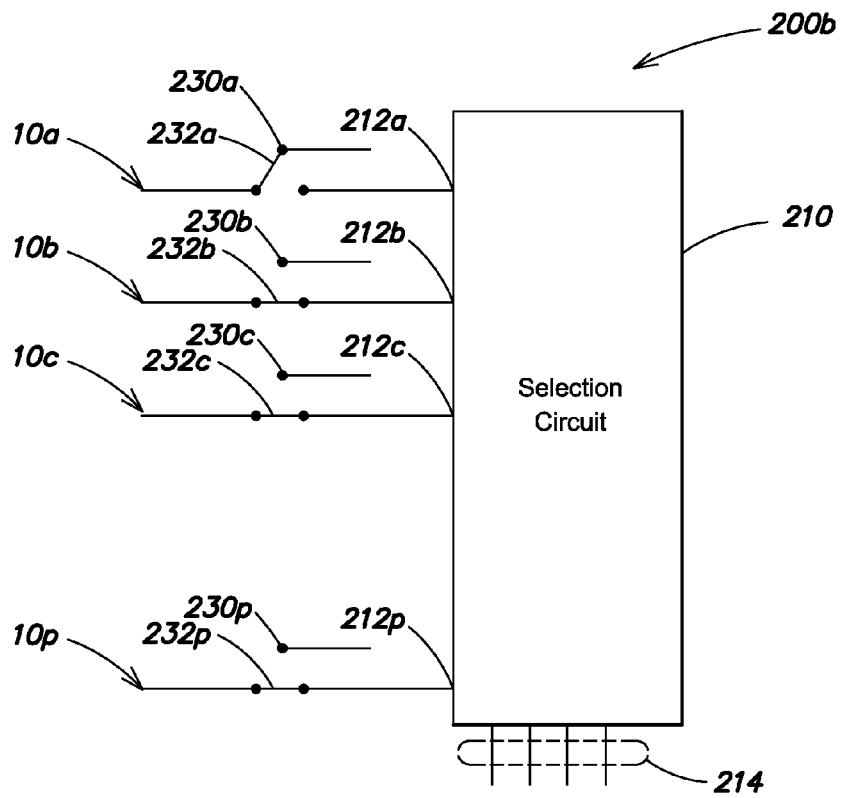
FIG. 2B illustrates an electrode signal acquisition circuit according to another embodiment of the present invention that is similar to that of FIG. 2A but includes the ability to permit one or more the ECG sensing electrodes to be used as a driven ground electrode.

FIG. 2B illustrates an alternative signal acquisition circuit that may be used with embodiments of the present invention to select, from among a plurality of ECG sensing electrodes, those pairings of electrodes that provide a desired ECG signal, in terms of signal-to-noise ratio, phase discrimination, or any other criteria, and provide those ECG signals to downstream circuitry for further signal conditioning, processing, analysis, and/or monitoring. The signal acquisition circuit 200b is substantially similar to that of signal acquisition circuit 200a described immediately above with respect to FIG. 2A, and thus, only the selection circuit 210 is shown in FIG. 2B, and the other portions of circuit 200a, such as the differential circuit 220, are not depicted. However, in addition to being able to select any pairings of ECG sensing electrodes, the signal acquisition circuit 200b additionally allows any one of the plurality of ECG sensing electrodes 10a-10p to be used as a driven ground electrode.

As known to those skilled in the art of signal processing, a driven ground electrode is frequently used to eliminate noise that may be common to many or all sensors, such as ECG sensing electrodes 10a-10p. Noise signals present on some or all of the sensors, such as the ECG sensing electrodes are summed, then inverted, and then injected into the driven ground circuitry. Where the sensors are ECG sensing electrodes that are attached to the body of a patient, the inverted signal may be actively driven onto the body of the patient where it is picked up by the ECG sensing electrodes, effectively cancelling out the noise that would normally be detected.

However, in a wearable medical device, such as the wearable medical device described with respect to FIGS. 1A-F, there may be instances where the driven ground electrode 12 that is used to transmit the driven ground signal to the body of the patient may have fallen off, lost contact with the body of the patient, or simply not be working appropriately. Indeed, even where the driven ground electrode 12 is in good contact with the body of the patient and working properly, the driven ground electrode may simply be located in a sub-optimal position. Where any of these conditions exist, one or more of the plurality of ECG sensing electrodes 10a-10p may be used as a driven ground electrode. This aspect of the present invention in now described in more detail with respect to FIG. 2B.

As shown in FIG. 2B, a plurality of signal pads 230 can be provided with each respective signal pad 230a-230p being electrically coupled to a driven ground circuit (not shown). A plurality of switches 232 are provided, with each respective switch 232a-p being electrically coupled between a respective ECG sensing electrode 10a-p and a respective input 212a-p of the selection circuit 210. Each switch 232a-p is capable of being in one of two positions. In a first position, the switch 232 electrically couples a respective ECG sensing electrode 10a-p to a respective input 212a-p of the selection circuit. In the second position, the switch 232 electrically couples the respective electrode 10a-p to a respective signal pad 230a-p that is electrically coupled to the driven ground circuit. For example, as illustrated in FIG. 2B, switch 232a is in a position such that the signal pad 230a is electrically coupled to ECG sensing electrode 10a, whereas each of switches 232b, 232c, . . . 232p are in a position such that ECG sensing electrodes 10b-10p are respectively electrically coupled to a respective input 212b-212p of the selection circuit 210. In this configuration, ECG sensing electrode 10a may be used as a driven ground electrode, where that use provides a better signal on others of the plurality of ECG sensing electrodes, where another driven ground electrode has lost contact or has poor contact with the body of the patient, or for any other reason.

Figure 2C:
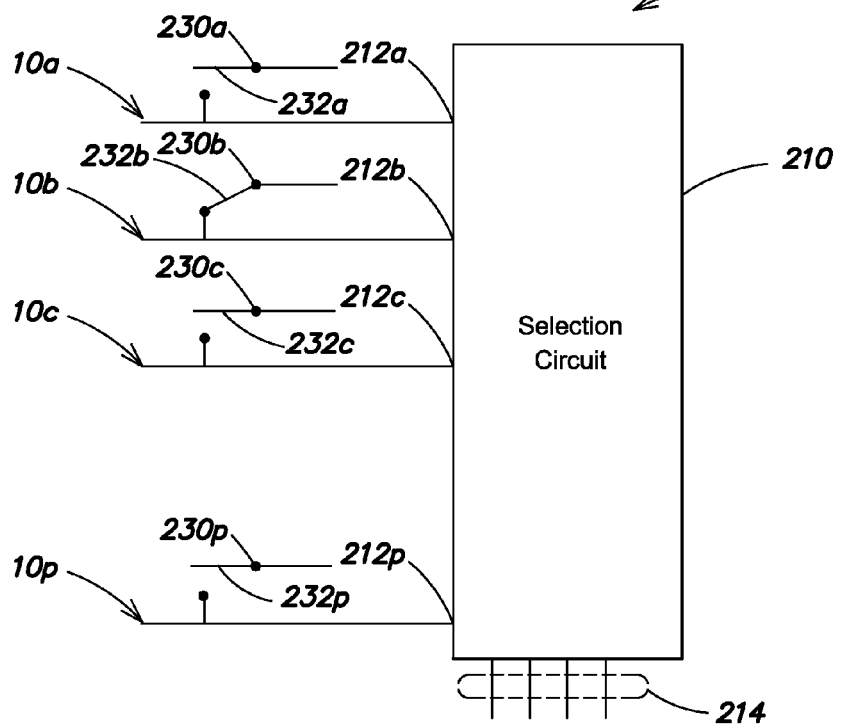
FIG. 2C illustrates an electrode signal acquisition circuit according to another embodiment of the present invention that is similar to that of FIG. 2B and permits one or more the ECG sensing electrodes to be used as a driven ground electrode.

FIG. 2C illustrates a further alternative signal acquisition circuit that may be used with embodiments of the present invention to select pairings of ECG sensing electrodes in a manner similar to that described above with respect to FIGS. 2A and 2B, and to allow any one of the plurality of ECG sensing electrodes to be used as a driven ground electrode in a manner similar to that described above with respect to FIG. 2B. The signal acquisition circuit 200c is substantially similar to that of signal acquisition circuit 200b described immediately above, and therefore, only the differences are described.

As in the signal acquisition circuit 200b, a plurality of signal pads 230 are provided with each respective signal pad 230a-230p being electrically coupled to a driven ground circuit (not shown). A plurality of switches 232 is also provided. Each respective switch 232a-p of the plurality of switches 232 is electrically coupled to a respective signal pad 230a-p of the plurality of signal pads 230, which in turn, is electrically coupled to a driven ground circuit (not shown). Each switch 232a-p is capable of being in one of two positions, opened and closed. In the open position, the driven ground signal on a respective signal pad 230a-p is an open circuit, and in the closed position, the switch 232 electrically couples a respective ECG sensing electrode 10a-p to a respective signal pad 230a-p. For example, as illustrated in FIG. 2C, switch 232a and each of switches 232c-232p is in an open position, and switch 232b is in a closed position, such that the signal pad 230b is electrically coupled to ECG sensing electrode 10b. This embodiment relies on the fact that the selection circuit 210 generally will have a relatively high input impedance, such that each of the inputs 212 may remain connected to an ECG sensing electrode 10 while that ECG sensing electrode is electrically coupled to the driven ground circuit, as the driven ground circuit will typically have a relative low output impedance. In this configuration, ECG sensing electrode 10b may be used as a driven ground electrode, where that use provides a better signal on others of the plurality of ECG sensing electrodes, where another driven ground electrode has lost contact or has poor contact with the body of the patient, or for any other reason.

It should be appreciated that in the embodiments of FIGS. 2B and 2C described above, more than one driven ground circuit may be provided. For example, ECG sensing electrode 10a could be used as a driven ground electrode for use with ECG sensing electrodes 10c, 10d, 10o, 10n, 10e, 10h, 10i, and 10l (see FIG. 1G), and ECG sensing electrode 10b could be used as a driven ground electrode for use with ECG sensing electrodes 10m, 10p, 10g, 10f, 10k, and 10j.

Figure 3:
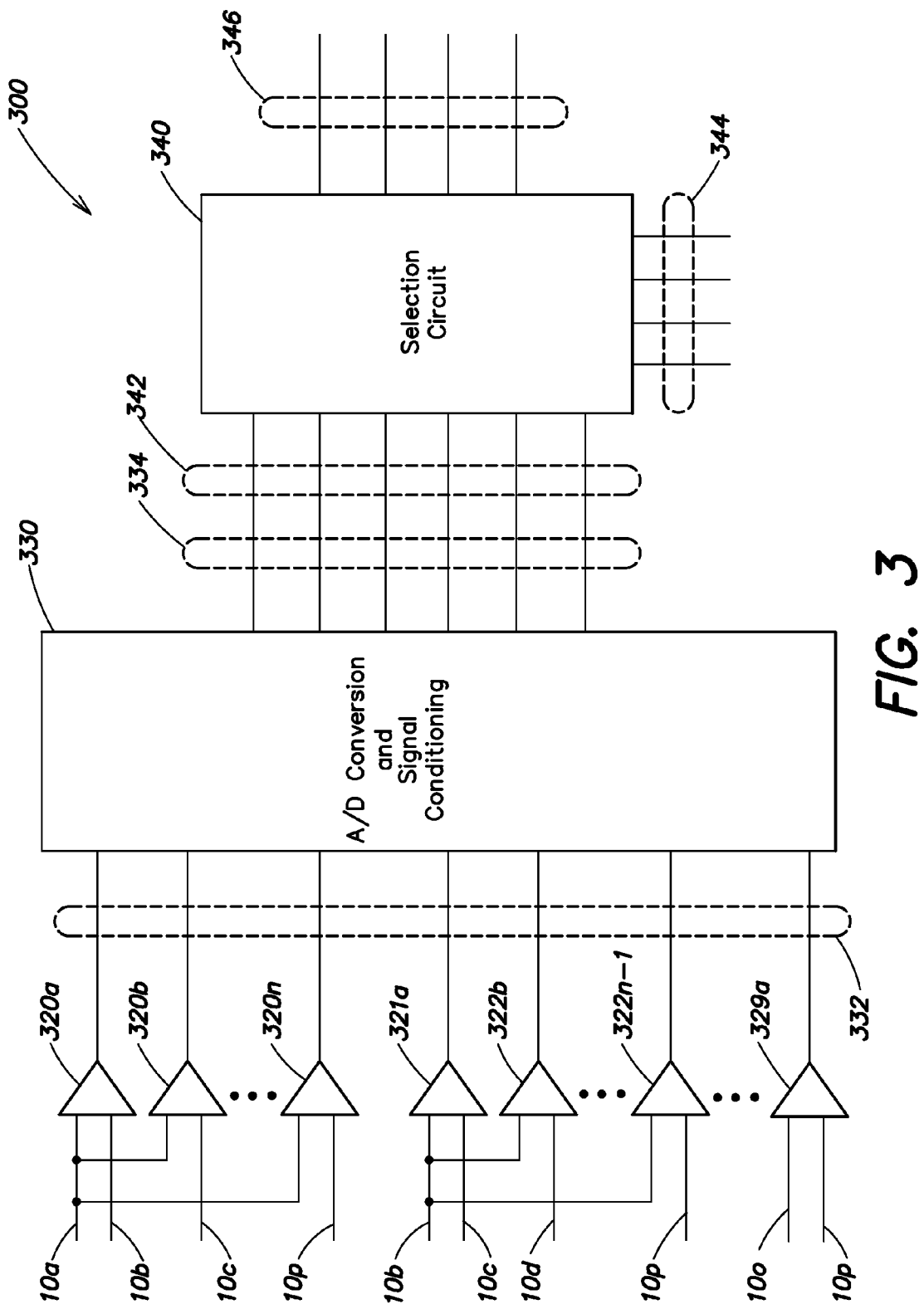
FIG. 3 illustrates an alternative electrode signal acquisition circuit that may be used with embodiments of the present invention.

FIG. 3 illustrates a signal acquisition circuit according to another embodiment of the present invention that may be used to acquire signals from different pairings of ECG sensing electrodes, or from different pairings of ECG sensing electrodes and a driven ground electrode, and provide those signals to downstream circuitry, such as an A/D conversion and signal conditioning block 330 of an arrhythmia monitoring and/or treatment system. As shown in FIG. 3, the signal acquisition circuit 300 includes a plurality of analog differential instrumentation amplifiers 320a-320n, 321a-321n-1, . . . 329a that are each configured to receive signals from different pairings of ECG sensing electrodes. For example, a first grouping of amplifiers 320a-320n may be configured to respectively pair each of ECG sensing electrodes 10b-10p (FIG. 1G) with ECG sensing electrode 10a, a second grouping of amplifiers 321a-321n-1 may be configured to respectively pair each of ECG sensing electrodes 10c-10p with ECG sensing electrode 10b, etc. Although not shown, each grouping of amplifiers may also compare a signal from a respective ECG sensing electrode with a driven ground electrode, or with each of a number of driven ground electrodes. In contrast to the signal acquisition circuit 200 of FIGS. 2A-C, individual signals from each of the different pairings of ECG sensing electrodes are provided directly to the inputs of a respective amplifier. As such, this embodiment may avoid noise or signal degradation caused by the selection circuit 210 being located prior to the differential circuit 220. Such selection circuitry may instead be provided after an analog-to-digital conversion and signal conditioning block, such as the analog-to-digital conversion and signal conditioning block 14 described with respect to FIGS. 2a-2c of the '669 patent. For example, as shown in FIG. 3, the analog differential output signals provided by each respective amplifier 320a-320n, 321a-321n-1, 329a may be provided to a respective input 332 of an A/D conversion and signal conditioning block 330 that digitizes and conditions the analog differential output signals. The digitized and conditioned signals provided on a respective output 334 of the A/D conversion and signal conditioning block 330 may then be provided to a respective input 342 of an output selection circuit 340 that operates in a manner similar to a multiple output multiplexer. Responsive to control signals provided to control inputs 344 of the selection circuit 340, the selection circuit selects, from among the plurality of digitized and conditioned signals, which of those digitized and conditioned signals to provide to a respective output 346 of the selection circuit for monitoring and/or analysis.

In accordance with an aspect of the present invention, each of the different pairings of ECG sensing electrodes 10 may be selected and their signals analyzed to identify those pairings of ECG sensing electrodes that provide a desired ECG signal, in terms of signal-to-noise ratio, phase discrimination, or any other criteria. Those pairings of ECG sensing electrodes providing the highest signal-to-noise ratio, a particular phase discrimination or a maximum phase discrimination, or those pairings of electrodes corresponding to particular planes may then be selected to provide those signals to a cardiac monitor, or to an arrhythmia detection system, such as that illustrated in FIGS. 2a-c of the '669 patent. For example, referring to FIG. 1G, if it were determined that the pairing of ECG sensing electrodes 10a and 10j, and 10c and 10d provided the highest quality signal (in terms of a high signal-to-noise ratio and maximum phase discrimination), but the pairing of ECG sensing electrodes 10a and 10b did not, the signal from ECG sensing electrode 10j would be paired with ECG sensing electrode 10a and the signals from these ECG sensing electrodes could be analyzed with respect to the signals from ECG sensing electrodes 10c and 10d.

It should be appreciated that embodiments of the present invention provide a cardiac monitoring system and/or a cardiac monitoring and arrhythmia detection system with the ability to select, from among a plurality of electrodes, those pairings of electrodes that provide the highest quality signal, a particular phase difference or a maximum phase discrimination, or any other criteria. With this ability to choose ECG sensing electrodes, the analyzer of the cardiac monitoring and arrhythmia detection system can, for example, be tuned to give the best orthogonal view and can provide more cardiac information than a single or dual channel sensing system. The analyzer can select multiple templates representing different phase angles between ECG sensing electrode leads, or templates representing different planes of view of the patient's heart. Each electrode channel can be auto correlated (compared to itself) or cross correlated (compared with other channels) in order to screen out noise and derive additional information.

Embodiments of the present invention can also return to the best axis positions if the overall electrode system was shifted at a later time, such as when the electrodes are configured as part of a wearable electrode belt or garment system. Because this multiple electrode configuration can select the electrodes with the best quality signal, the number of alarms due to ECG noise and fall-off can be reduced. Another byproduct of a cleaner ECG signal is a reduction in false detections. By checking multiple electrodes, and finding that the majority are sensing the same thing, embodiments of the present invention can increase the confidence level of the detection algorithm. In addition, each time the electrode belt or garment is worn, the electrodes may move to a slightly different location, resulting in a change to the ECG signal. With multiple electrode configurations, the detection system can scan the multiple paths and select the highest quality signals. Furthermore, by providing redundancy to the sensing system, this multiple electrode configuration helps to improve the overall system reliability. A fault in one or more channels can be tolerated because there are other working channels. These and other aspects of the present invention are now described with respect to FIGS. 4-8.

Figure 4:
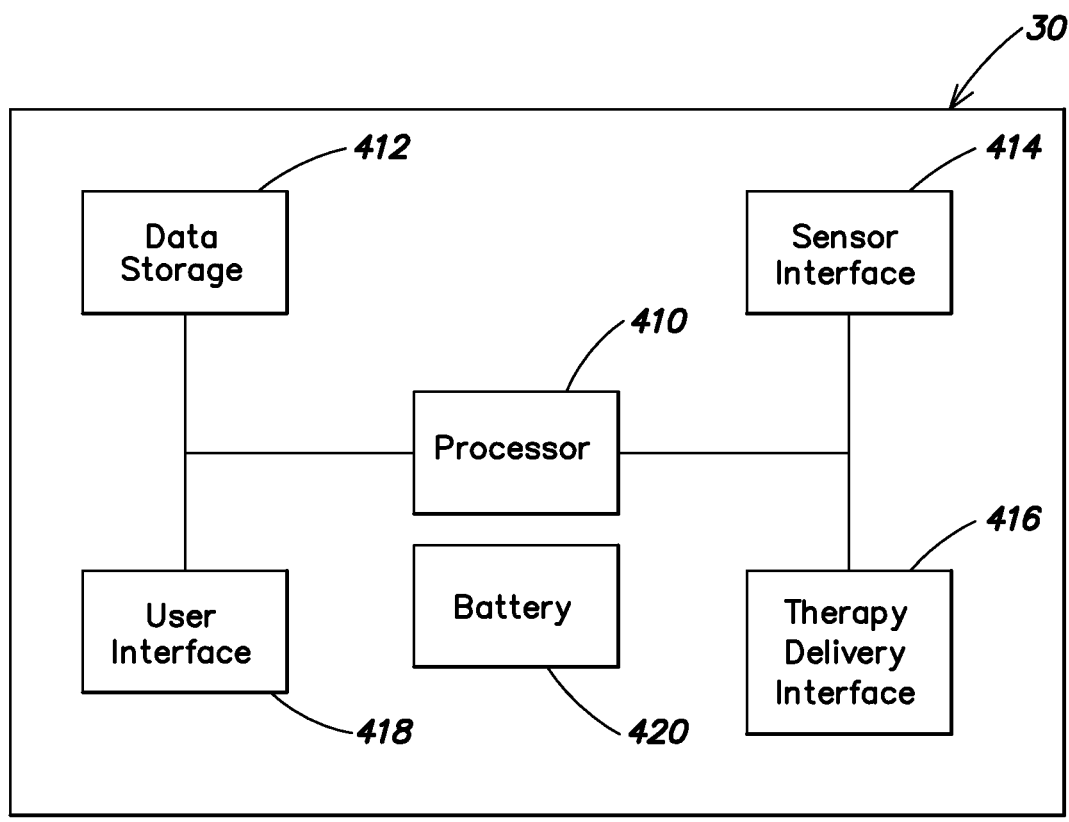
FIG. 4 is a functional block diagram of a control unit that may be used with embodiments of present invention.

FIG. 4 functionally illustrates a control unit, such as the control unit 30 depicted in FIGS. 1A-F that may be used by a portable medical device, such as a cardiac monitor or a wearable defibrillator, in accordance with the present invention. As shown, the control unit 30 includes at least one processor 410, a battery 420, a data storage 412, a sensor interface 414, a therapy delivery interface 416, and a user interface 418. The battery 420 may be a rechargeable three cell 2200 mAh lithium ion battery pack that provides electrical power to the other device components. The data storage 412, the sensor interface 414, the therapy delivery interface 416, and the user interface 418 are coupled to the at least one processor 410. The data storage 412 includes a computer readable and writeable data storage medium configured to store non-transitory instructions and other data, and can include both nonvolatile storage media, such as optical or magnetic disk, ROM or flash memory, as well as volatile memory, such as RAM. The instructions may include executable programs or other code that can be executed by the at least one processor 410 to perform any of the functions described here below.

The therapy delivery interface 416 couples one or more therapy delivery devices, such as defibrillator therapy electrodes 12a-c (FIG. 1E), to the at least one processor 410. Where the control unit is used solely for monitoring a patient's cardiac condition, the therapy interface 416 and associated defibrillation therapy electrodes may be omitted. The user interface 418 includes a combination of hardware and software components that allow the control unit 30 to communicate with an external entity, such as a user. These components are configured to receive information from actions such as physical movement, verbal intonation or thought processes. In addition, the components of the user interface 418 can provide information to external entities, for example, in a manner such as described in U.S. Pat. No. 6,681,003, which is incorporated herein by reference. Examples of the components that may be employed within the user interface 418 include keyboards, mouse devices, trackballs, microphones, electrodes, touch screens, printing devices, display screens and speakers.

The sensor interface 414 couples the at least one processor 410 to a plurality of physiological sensors, such as the plurality of ECG sensing electrodes 10. In some embodiments, the sensor interface 414 may also couple the at least one processor 410 to other physiological sensors, such as activity sensors, pulse oxygen sensors, temperature sensors, respiratory rate sensors, thoracic impedance sensors, blood pressure sensors, acoustic sensors, etc. The sensor interface 414 can include a signal acquisition circuit, such as the signal acquisitions circuits 200 and 300 described above with respect to FIGS. 2A-C and 3, or the signal acquisition circuits 900, 1000, and 1100 described further below with respect to FIGS. 9-11, to select, from among the plurality of ECG sensing electrodes and/or other physiological sensors, those that provide a desired signal, in terms signal-to-noise ratio, phase discrimination, or any other criteria.

Although not illustrated in FIG. 4, the control unit 30 may include additional components and or interfaces, such as a communication network interface (wired and/or wireless), and the at least one processor 410 may include a power conserving processor arrangement such as described in co-pending application Ser. No. 12/833,096, titled SYSTEM AND METHOD FOR CONSERVING POWER IN A MEDICAL DEVICE, filed Jul. 9, 2010 (now U.S. Pat. No. 8,904,214, hereinafter "the '214 patent"), and incorporated by reference herein in its entirety. For example, as described in the '214 patent, the at least one processor 410 may include a general purpose processor, such as an Intel® PXA270 processor that is coupled to a critical purpose processor, such as a Freescale™ DSP56311 Digital Signal Processor (DSP). The general purpose processor can be configured to perform non-critical functions that do not require real time processing, such as interfacing with the communication network interface and the user interface, while the critical purpose processor is configured to perform critical functions that require real time processing, such as the sampling and analysis of ECG information, the charging of the capacitors to a particular voltage, and the generation and/or delivery of therapeutic defibrillating pulses. It should be appreciated that in some embodiments, the functionality of the at least one processor may be implemented in a Field Programmable Gate Array (FPGA), one or more Programmable Logic Devices (PLDs), a Complex PLD (CPLD), or custom Application Specific Integrated Circuit (ASIC).

FIGS. 5-8 illustrate a number of different processes that may be performed by the at least one processor 410 of the control unit 30 to improve the monitoring and analysis of cardiac activity, to improve the detection of cardiac abnormalities, and to reduce the number of false detections and fall-off alarms in accordance with embodiments of the present invention.

Figure 5:
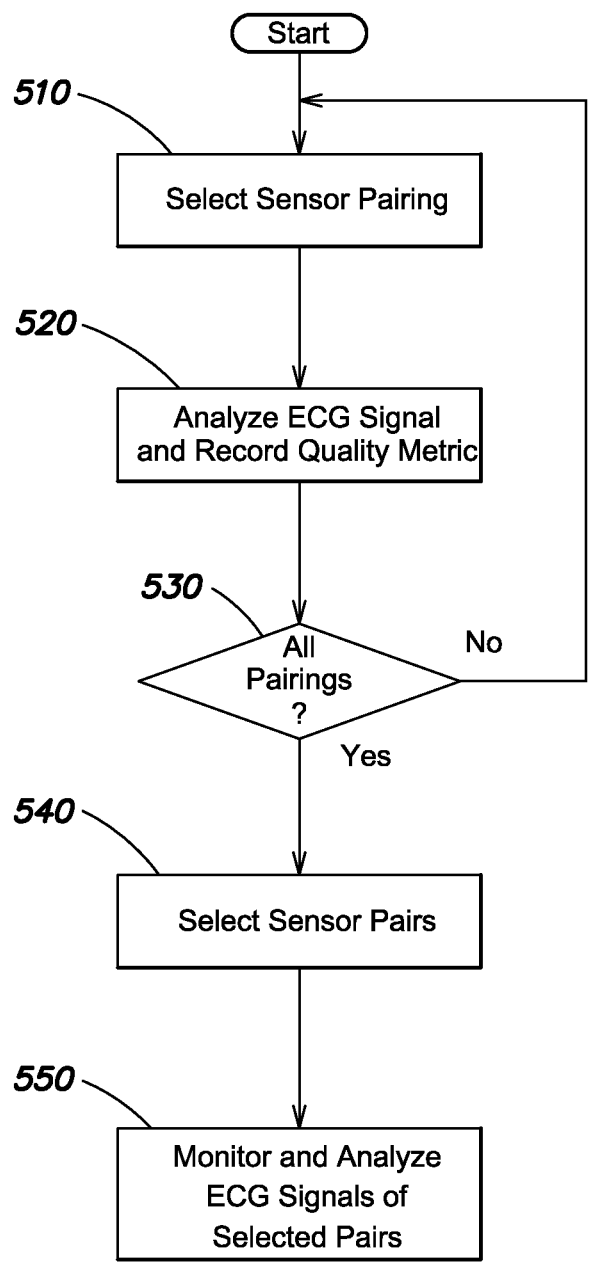
FIG. 5 is a flow diagram of an electrode selection process that may be performed by at least one processor of the control unit of FIG. 4.

FIG. 5 illustrates a selection process that may be executed by the at least one processor 410 of the control unit 30 to select, from among a plurality of ECG sensing electrodes 10, those providing a highest quality ECG signal, in terms of signal-to-noise ratio and maximum phase discrimination, in accordance with one embodiment of the present invention. In act 510, the at least one processor 410 selects a pair of ECG sensing electrodes to monitor. As discussed previously, this may be performed by the at least one processor sending appropriate control signals to selection circuit 210, 340.

In act 520, the at least one processor analyzes the ECG signal obtained from the selected pair of ECG sensing electrodes and records information identifying the selected pair of ECG sensing electrodes and a metric indicative of the quality of the ECG signal provided therefrom. Although a number of different criteria may be used to identify the quality of the ECG signal, in one embodiment, those ECG signals having a highest signal-to-noise ratio and a maximum phase discrimination are assigned a higher quality metric than those pairings that do not.

In act 530, the at least one processor determines whether each of the possible pairings of ECG sensing electrodes have been selected and analyzed. Where it is determined that all the possible pairings of ECG sensing electrodes have been selected and analyzed, the process proceeds to act 540. Alternatively, where it is determined that fewer than all of the possible pairs of ECG sensing electrodes have been selected and analyzed, the process returns to act 510, where a next sensor pairing is selected. Acts 510 through 530 are then performed for each of the possible pairings of ECG sensing electrodes.

In act 540, the at least one processor selects, from among the plurality of different pairings of ECG sensing electrodes, those pairs of ECG sensing electrodes having the highest quality metric. It should be appreciated that the number of different pairings of ECG sensing electrodes that are selected in act 540 will depend on the number of different channels provided at the output 226 of the differential circuit 220 (FIG. 2A) or at the output 346 of the selection circuit 340 of FIG. 3. In general, a minimum of two channels would be selected in act 540, and in most implementations, at least four different channels would be selected. In some embodiments, the number of channels provided may correspond to each unique pairing of electrodes.

In act 550, the at least one processor monitors and analyzes the ECG signals provided by the selected pairings of ECG sensing electrodes. The act of monitoring and analyzing the ECG signals provided by the selected ECG sensor pairs (i.e., act 550) may continue until the terminated by removal and/or power down of the wearable medical device.

In accordance with one embodiment of the present invention, the selection process described with respect to FIG. 5 may be performed each time the electrode system 100 is powered on to account for any potential repositioning of the plurality of electrodes 10 on the body of the patient. Thus, for example, when a garment 20a-20c incorporating an electrode system 100 is removed from the body of the patient to allow the patient to shower, for service, or for any other reason, and then returned to a position on the patient's body, the positioning of some or all of the ECG sensing electrodes may change from their prior position. By re-executing the selection process of FIG. 5, the electrode system may select those pairings of ECG sensing electrodes that provide the highest quality ECG signals, irrespective of whether those pairings of ECG electrodes are the same, or different from those selected previously. In certain implementations, an initial pairing of ECG sensing electrodes may be based upon those that were previously selected in act 540. For example, in response to a garment incorporating an electrode system 100 being removed from and returned to the body of a patient, the electrode system may initially select pairings of ECG sensing electrodes based upon those that were selected prior to removal of the garment in act 540. That initial selection may then be confirmed by re-executing the selection process of FIG. 5.

It should be appreciated that the selection process described with respect to FIG. 5 may be re-executed, either at periodic intervals (e.g., every half hour), or in response to another sensor, such as an activity sensor, indicating strenuous physical activity, to ensure the optimal pairings of ECG sensing electrodes are selected. By re-executing the selection process, either periodically, or in response to detected physical activity, embodiments of the present invention can ensure that those pairings of ECG sensing electrodes providing the highest quality ECG are identified and used for monitoring and analysis.

Although the selection process of FIG. 5 was described as selecting those pairs of ECG sensing electrodes providing the highest quality ECG signal, in terms of signal-to-noise ratio and maximum phase discrimination, it should be appreciated that other criteria may be used. For example, the process described with respect to FIG. 5 may be modified to include an act of selecting a desired template prior to act 510. The desired template may, for example, reflect different phase angles between ECG sensing electrodes that are desired to be monitored. The acts 510 and 520 of selecting and analyzing different ECG sensing electrode pairings could thus select, from among the plurality of ECG sensing electrodes, those pairs of ECG sensing electrodes that provide the highest signal-to-noise ratio from among those pairings that meet the desired phase angle(s) of the template. It should be appreciated that other criterion, other than phase angle, may be reflected in a template, and that multiple templates may be provided and/or selected. For example, one template may correspond to different pairings of ECG sensing electrodes that correspond to different planes intersecting the patient's heart, while another template may correspond to different pairing of ECG sensing electrodes that are all co-located in the same plane.

Figure 6:
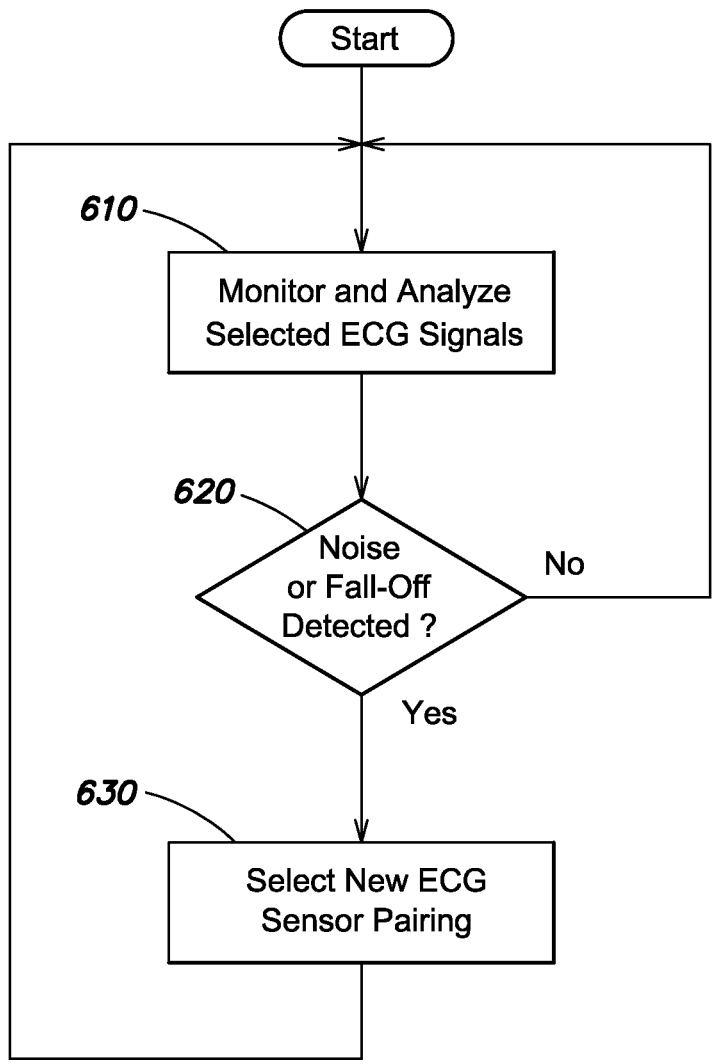
FIG. 6 is a flow diagram of a noise/fall-off detection process that may be executed by the at least one processor of the control unit of FIG. 4.

FIG. 6 illustrates a noise/fall-off detection process that may be executed by the at least one processor 410 of the control unit 30 (FIG. 4) in accordance with an aspect of the present invention to improve the quality of monitoring and analysis of ECG signals and/or to reduce the number of fall-off alarms. In act 610 the at least one processor monitors and analyzes selected ECG signals from different pairings of ECG sensing electrodes. The pairings of ECG sensing electrodes that are monitored and analyzed in act 610 may have been previously selected based upon a selection process such as that described with respect to FIG. 5. In act 620, the at least one processor makes a determination as to whether there is noise in the ECG signal of a selected pairing of ECG sensing electrodes, or whether there has been a fall-off or at least partial loss of contact with the body of the patient by a selected pairing of ECG sensing electrodes. Where it is determined in act 620 that there is no appreciable noise or a diminished signal or a lack of signal on any of the selected pairings of ECG sensing electrodes, the at least one processor returns to act 610 and continues monitoring the selected ECG signals. Alternatively, where it is determined that there is appreciable noise or a diminished signal or lack of signal from one of the selected pairings of ECG sensing electrodes, the process proceeds to act 630.

In act 630 the at least one processor 410 selects a new pairing of ECG sensing electrodes to replace the pairing in which increased noise, or a diminished ECG signal was detected. Act 630 may be performed in a manner similar to the selection process described with respect to FIG. 5. In act 630, each of the possible pairings of ECG sensing electrodes may be re-evaluated to select those pairings of ECG electrodes to be monitored. Alternatively, those selected pairings of ECG sensing electrodes in which noise or fall-off was not detected may be retained as selected pairings, and the remaining ECG sensing electrodes evaluated to identify and select a pairing of ECG sensing electrodes to replace the pairing in which noise or fall-off was detected. In response to the selection of a new pairing of ECG sensing electrodes, or a number of new pairings, the process returns to monitoring an analyzing ECG signals in act 610.

Although not shown in FIG. 6, in response to the detection of noise or fall-off in a selected pairing of ECG sensing electrodes, the at least one processor 410 may conduct additional tests on the selected pairing. For example, the at least one processor may pair each ECG sensing electrode of the selected pair with a driven ground electrode to identify which of the ECG sensing electrodes of the selected pair may have a noise issue or may have at least partially lost contact with the body of the patient. The at least one processor 410 may also send a message to the user of portable medical device (or a bystander) via the user interface 418 to notify the user that one or more of the ECG sensing electrodes of the selected pairing may have a noise issue or may have at least partially lost contact with the body of the patient, and may further request the user to reposition the ECG sensing electrodes of the selected pairing.

Figure 7:
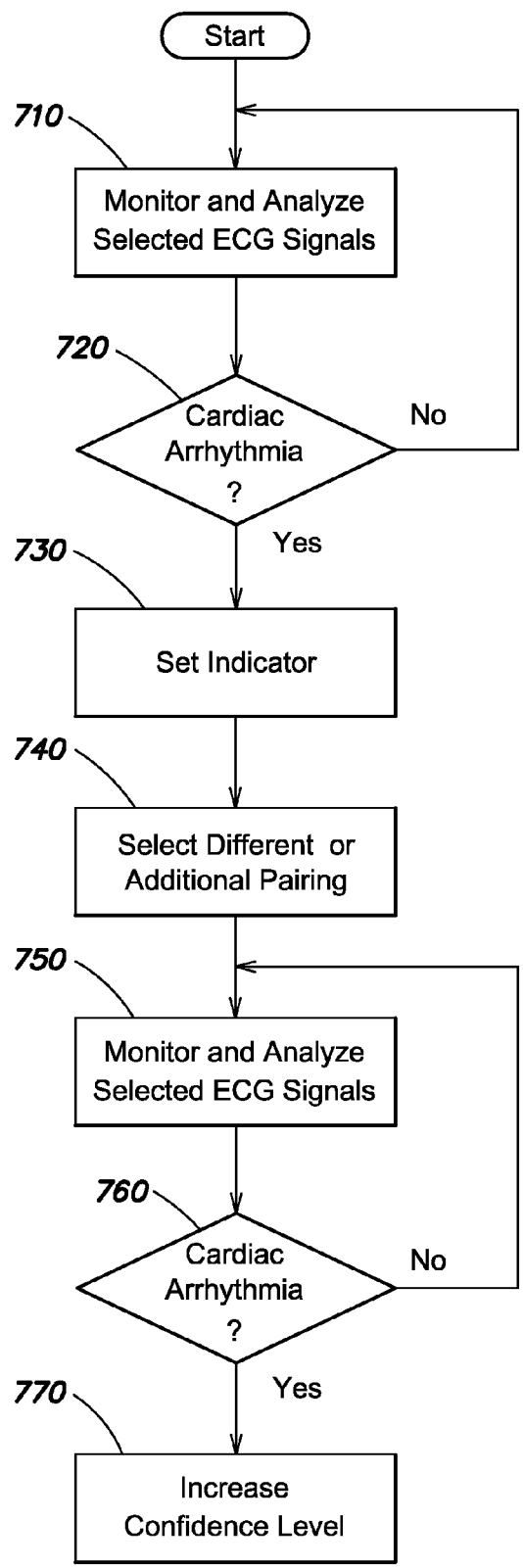
FIG. 7 is a flow diagram of a monitoring and analysis routine that may be executed by the at least one processor of the control unit of FIG. 4.

FIG. 7 illustrates monitoring and analysis routine that may be executed by the at least one processor 410 of the control unit 30 to improve the detection of cardiac arrhythmias and reduce the number of false detections. In act 710 the at least one processor monitors and analyzes selected ECG signals from different pairings of ECG sensing electrodes. The pairings of ECG sensing electrodes that are monitored and analyzed in act 710 may have been previously selected based upon a selection process such as that described with respect to FIG. 5. In act 720 a determination is made as to whether a cardiac arrhythmia has been detected. Where it is determined in act 720 that a cardiac arrhythmia, such as ventricular tachycardia or ventricular fibrillation, has not been detected, the process returns to act 710 and continues to monitor and analyze the selected ECG signals. Alternatively, where it is determined in act 720 that a cardiac arrhythmia has been detected, the at least one processor proceeds to act 730 wherein the at least one processor sets a flag or indicator identifying that a cardiac arrhythmia has been detected, with the at least one processor proceeding to act 740.

In act 740, the at least one processor 410 selects a different or additional pairing of ECG sensing electrodes to monitor, to identify whether the determined arrhythmia is also present in the ECG signals from other pairings of ECG sensing electrodes. The additional or different pairings of ECG sensing electrodes may be based upon the selection process described previously with respect to FIG. 5. For example, the additional or different pairings of ECG sensing electrodes that are selected in act 740 may be one or more of those pairings that provides the next highest signal quality level other than those that were selected in act 540 of FIG. 5. In act 750, the at least one processor continues to monitor and analyze the selected ECG signals, including those from additional or different pairings of ECG sensing electrodes selected in act 740.

In act 760, the at least one processor 410 again determines whether a cardiac arrhythmia has been detected, based upon the ECG signals monitored in act 750. Where it is determined that a cardiac arrhythmia has not been detected in the different or additional pairings, the at least one processor may simply return to act 750 and continue to monitor the selected ECG signals. However, where it is determined in act 760 that a cardiac arrhythmia, such as ventricular tachycardia or ventricular fibrillation has been detected, the at least one processor may proceed to act 770. In act 770, in response to detecting that the cardiac arrhythmia is still present, or is also present on the selected additional or different pairings of ECG sensing electrodes, the at least one processor increases a confidence level of the indicator or flag set in act 730. Although not depicted in FIG. 7, in response to the confidence level being above a certain threshold, and the cardiac arrhythmia being a type of cardiac arrhythmia for which defibrillation is an appropriate treatment, the at least one processor 410 may execute one or more instructions that result in defibrillation being applied to the body of the patient via the therapy delivery interface 416. In accordance with this aspect of the present invention, by examining other pairings of ECG sensing electrodes in response to a detected cardiac arrhythmia, the detection specificity of cardiac arrhythmias may be increased and the number of false detections of cardiac malfunction may be reduced.

Figure 8:
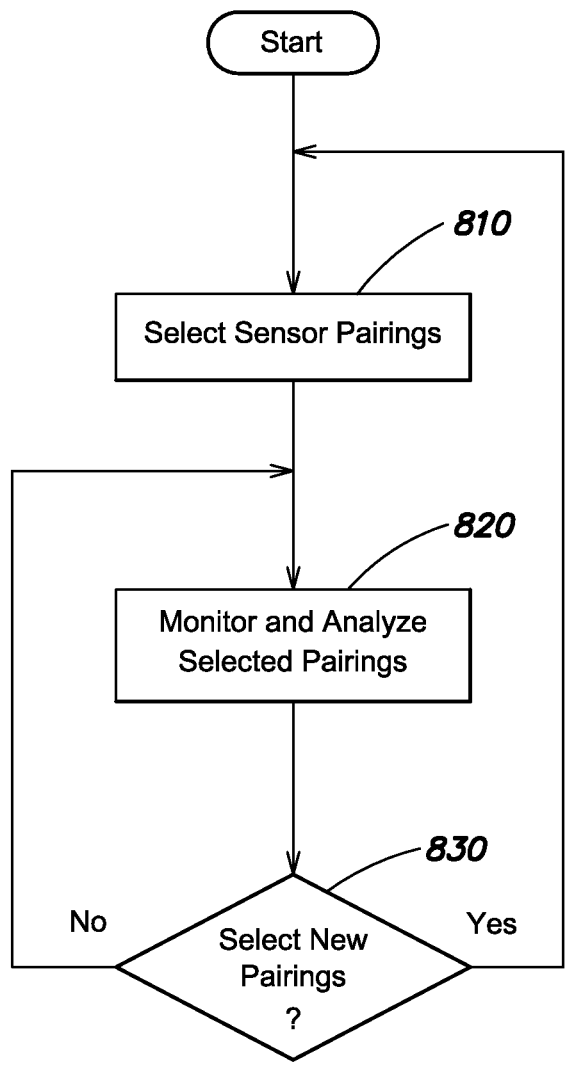
FIG. 8 is a flow diagram of an alternative monitoring and analysis routine that may be executed by the at least one processor of the control unit of FIG. 4.

FIG. 8 illustrates a monitoring and analysis routine in accordance with another embodiment of the present invention that may be executed by the at least one processor 410 of the control unit 30 to improve the monitoring and analysis of cardiac activity. In act 810 the at least one processor monitors and analyzes selected ECG signals from different pairings of ECG sensing electrodes. The pairings of ECG sensing electrodes that are monitored and analyzed in act 810 may have been previously selected based upon a selection process such as that described with respect to FIG. 5, or they may have been selected for other reasons. For example, the pairings of ECG electrodes may not provide the highest quality ECG signal of all of the ECG sensor pairs, but may correspond to a particular plane or planes, or to a particular position relative to the heart.

In act 820, the at least one processor 410 monitors and analyzes the ECG signals provided by the selected pairings of ECG sensing electrodes. In act 830 a determination is made as to whether to select new pairs of ECG sensing electrodes to monitor. The determination as to whether to select new pairs of ECG sensing electrodes may be based upon a number of different criteria, including the number of channels that are capable of being monitored and analyzed at a time, the type of information that is sought, the stage of the cardiac cycle (e.g., the diastolic stage, or the systolic stage), the position of the ECG sensing electrodes relative to the heart and/or the stage of depolarization or repolarization of the heart (e.g., as indicated by PQRST waveform of the ECG signals), etc. For example, where the control unit 30 is capable of simultaneously monitoring three different channels and the plurality of ECG sensing electrodes 10 includes 12 ECG sensing electrodes, three pairings of ECG sensing electrodes (including six distinct ECG sensing electrodes) may be monitored and analyzed during a first time interval, and the remaining three pairings of ECG sensing electrodes that were not monitored and analyzed during the first interval may be monitored and analyzed during a second and subsequent time interval. Alternatively, where the control unit is capable of simultaneously monitoring three different channels and the plurality of ECG sensing electrodes 10 includes 16 ECG sensing electrodes (as shown in FIG. 1G), three different pairings of ECG sensing electrodes including ECG sensing electrode pairs 10o-10p, 10c-10d, 10m-10n may be monitored and analyzed during a first time interval, three different pairings of ECG sensing electrodes including ECG sensing electrode pairs 10g-10h, 10k-10l, and 10b-10a may be monitored during a second interval, and three different pairs of ECG sensing electrodes including ECG sensing electrodes pairs 10j-10i, 10f-10e, and 10o-10p may be monitored and analyzed during a third time interval. In this manner, the selected pairings of ECG electrodes may sweep about the circumference of the heart. It should be appreciated that where the number of channels that can be simultaneously monitored by the control unit 30 are sufficient to monitor all pairings of ECG sensing electrodes, or all unique pairings of ECG sensing electrodes, then all such pairings may be monitored simultaneously.

Accordingly, in act 830, where it is determined that a new or different pairing of ECG sensing electrodes are to be monitored and analyzed, the monitoring and analysis routine returns to act 810 wherein those new or different pairings of ECG sensing electrodes are selected (act 810) and monitored and analyzed (act 820). Alternatively, where it is determined in act 830 that a new or different pairing of ECG sensing electrodes is not desired, the routine returns to act 820 and continues monitoring the pairings of previously selected ECG sensing electrodes.

Figure 9:
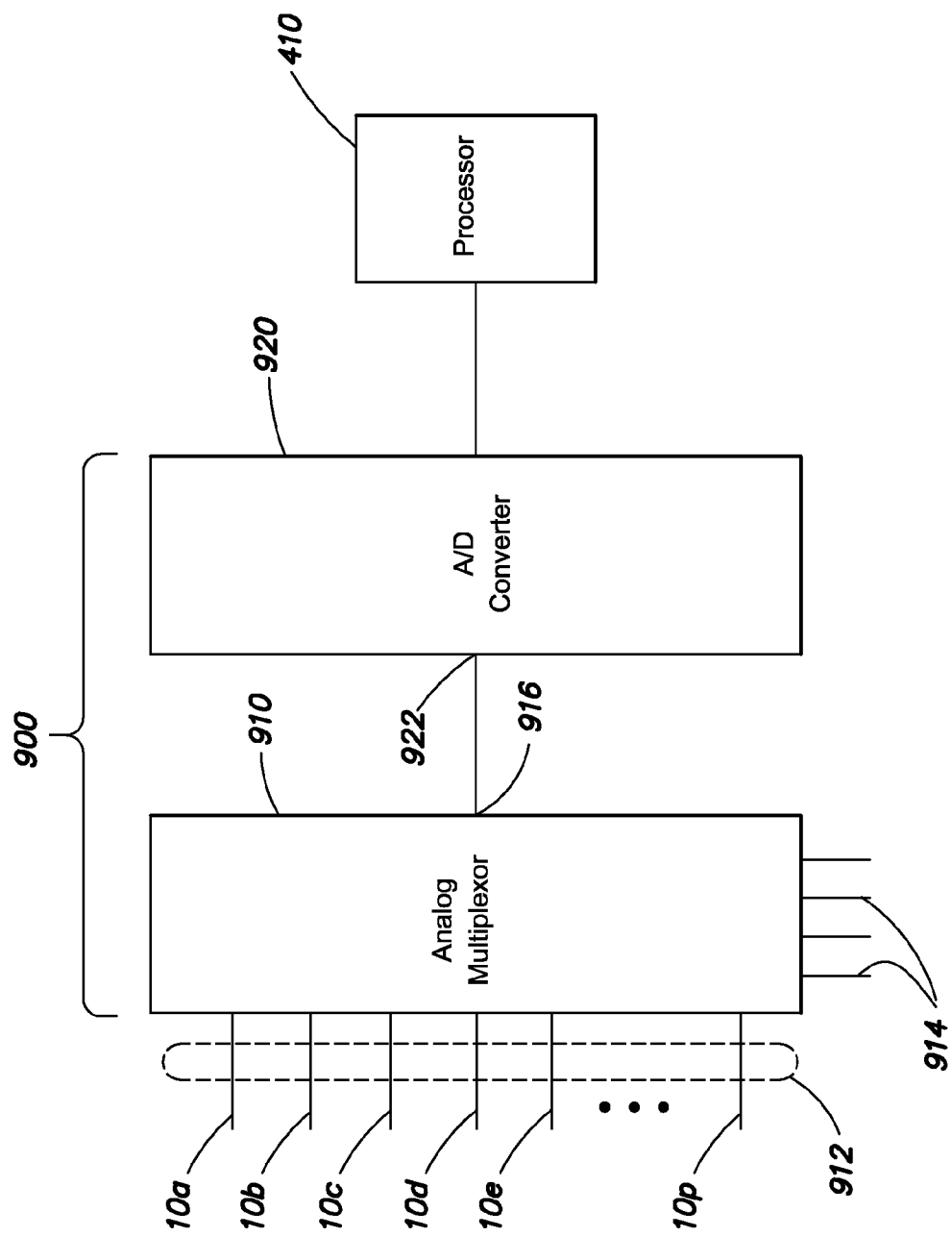
FIG. 9 illustrates a further alternative signal acquisition circuit that may be used with embodiments of the present invention.

FIG. 9 illustrates an alternative signal acquisition circuit that may be used with embodiments of the present invention to select, from among a plurality of ECG sensing electrodes, those pairing of electrodes that provide a desired ECG signal, in terms of signal-to-noise ratio, phase discrimination, or any other criteria, and provide those ECG signals to downstream circuitry for further signal conditioning, processing, analysis, and/or monitoring. In contrast to the embodiments described previously with respect to FIGS. 2A-C and 3, the signal acquisition circuit 900 does not include any differential amplifiers but instead generates differential ECG signals corresponding to selected pairings of ECG sensing electrodes in software executed by a processor, such as the at least one processor 410 described previously with respect to FIG. 4.

As shown, the signal acquisition circuit 900 includes an analog multiplexor 910 and an analog-to-digital (A/D) converter 920. Signals from each of the plurality of ECG sensing electrodes 10a-10p are provided to a respective input of a plurality of inputs 912 of the analog multiplexor 910. The analog multiplexor has an output 916 that is electrically coupled to an input 922 of the A/D converter 920. The analog multiplexor 910 includes a plurality of control inputs 914 to select which one of the plurality of signals received from a respective ECG sensing electrode 10a-10p is provided to the input 922 of the of the A/D converter 920. The A/D converter 920 receives the selected signal from the selected one of the plurality of ECG sensing electrodes and converts that analog ECG sensor signal to a digital signal. To ensure adequate resolution for the processing of the digitized signals that is performed by the at least one processor 410, the A/D converter 920 may be a 24 bit A/D converter, although an A/D converter with fewer bits may be used. In general, the sampling rate of the A/D converter 920 should be at least N times the desired sampling rate of the ECG signal, where N is the number of ECG sensing electrodes that are desired to be monitored. For example, where it is desired to monitor ECG signals provided by each of three pairs of ECG sensing electrodes at a sampling rate of 400 Hz, the A/D converter 920 should have a sampling rate in excess of 2.4 KHz. It should be appreciated that higher sampling rates may of course be used.

Although not shown in FIG. 9, each of the signals from a respective ECG sensing electrode 10-10p may first be buffered, filtered, and/or amplified prior to being received at a respective input of the analog multiplexor 910. For example, each of the signals received from a respective one of the plurality of ECG sensing electrodes 10a-p may be provided to the input of a high impedance buffer so that the analog multiplexor and the A/D converter to do not load down the respective ECG sensing electrode. The output of a respective buffer may be low-pass filtered (i.e., anti-aliased) to ensure that any frequency components of the signal are below the Nyquist frequency of the A/D converter 920, and the filtered signal provided to a low-noise and low to moderate gain amplifier to amplify the signal before that signal is provided to a respective input of the analog multiplexor 910. As would be appreciated by one skilled in the art, the combination of buffering, filtering, and/or amplifying the signal received from each of the plurality of ECG sensing electrodes may be performed in multiple and distinct stages (e.g., a high impedance buffer stage followed by a filtering stage and one or more amplification stages), or some of the stages, such as the buffering and amplification stages may be performed in a single stage (e.g., a high impedance low-noise amplifier with low to moderate gain). In some embodiments, the amplification stage may be programmable by the at least one processor 410.

In accordance with one embodiment, the analog multiplexer 910 may be a conventional analog multiplexer, available from companies such as Analog Devices, Inc. of Norwood Mass., in which control signals received on the control inputs of the analog multiplexer select which one of the signals received on a respective input of the multiplexer is provided to the output. The A/D converter 920 converts the received signal to a digital signal and provides the converted digital signal to the at least one processor 410. The at least one processor is configured to control the multiplexor 910 and the A/D converter 920 to sample and convert each of the signals received from a respective ECG sensing electrode over a different time interval and provide the converted signals to the at least one processor 410. Dependent upon which of the plurality of ECG sensing electrodes 10*a-p* are selected to be paired with one another, the at least one processor 410 takes the two selected digital signals, inverts one of them, and digitally sums the signals, effectively performing the same functionality as the differential instrumentation amplifiers described with respect to FIGS. 2A-C and 3 above. The selection, inversion, and summing of selected pairs of digital signals may be performed for any pairing of ECG sensing electrodes. The digitally summed signals may then be processed to monitor the patient's ECG signals, to detect any arrhythmic cardiac condition, or both. It should be appreciated that which of the pairs of ECG sensing electrodes to pair and monitor may be performed in software by the at least one processor in a manner similar to that shown in FIG. 5. Each of the digitized signals may be compared to one another for maximum phase difference, or a specific phase difference, or for any other criterion. Those pairings of ECG sensing electrodes may then be selected and monitored and analyzed in the manner described above.

In accordance with an alternate embodiment, the analog multiplexer 910 may be an analog sample-and-hold multiplexer that is capable of simultaneously sampling signals received from each of the plurality of ECG sensing electrodes over a first time period, and then providing each of the plurality of sampled signals to the A/D converter 920 during subsequent time periods. In this embodiment, the at least one processor 410 is configured to control the analog multiplexer 910 and the A/D converter 920 to sample and hold the signals received from each of the plurality of ECG sensing electrodes 10*a-p* over a first time period, and provide each, or selected ones, of the sampled signals to the A/D converter 920 to be converted to digital signals and provided to the at least one processor over subsequent time periods. As in the embodiment described above, dependent upon which of the plurality of ECG sensing electrodes 10*a-p* are selected to be paired with one another, the at least one processor 410 takes the two selected digital signals, inverts one of them, and digitally sums the signals, effectively performing the same functionality as the differential instrumentation amplifiers described with respect to FIGS. 2A-C and 3 above. The selection, inversion, and summing of selected pairs of digital signals may be performed for any pairing of ECG sensing electrodes. The digitally summed signals may then be processed to monitor the patient's ECG signals and/or to detect any arrhythmic cardiac condition.

Figure 10:
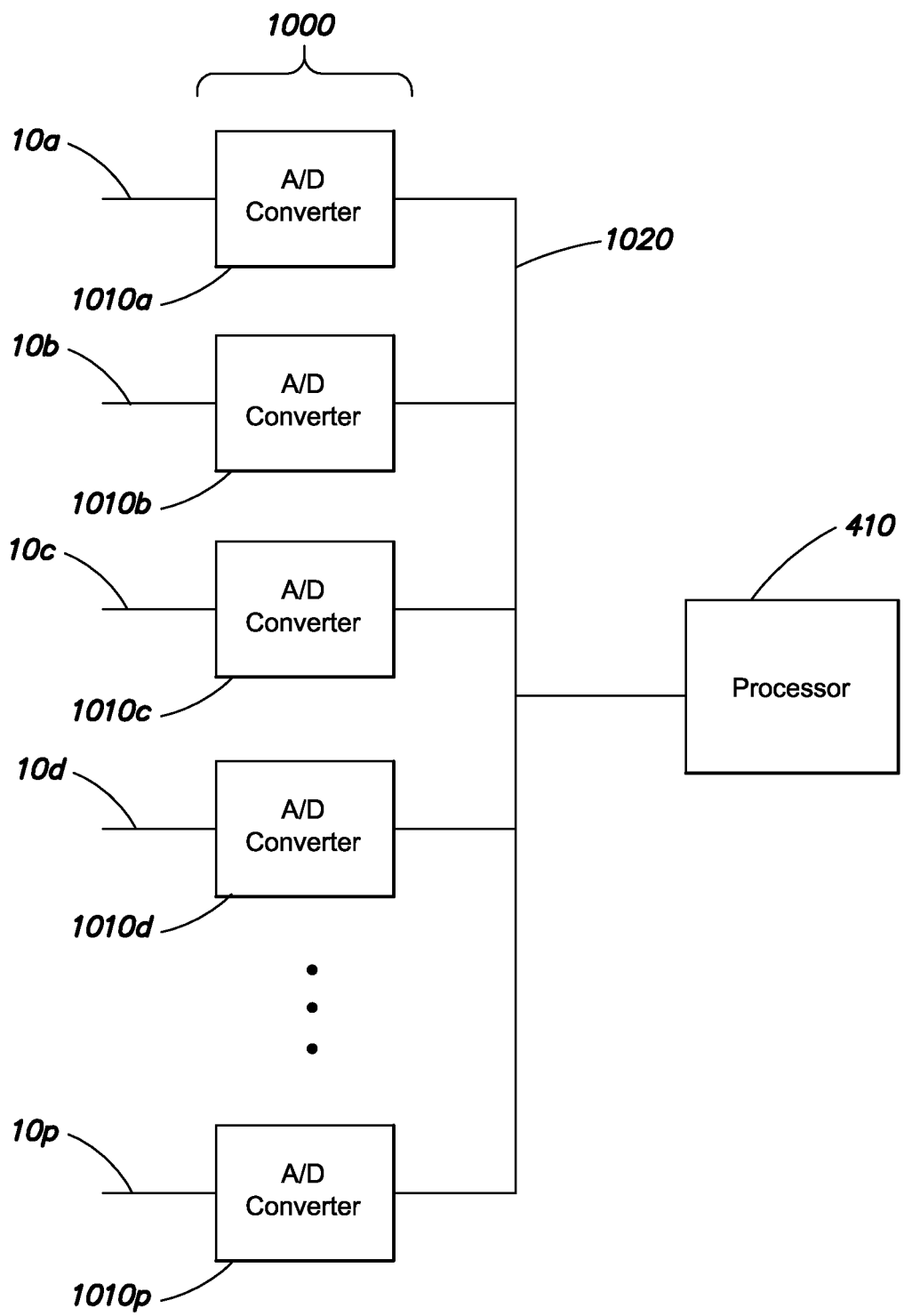
FIG. 10 illustrates yet another alternative signal acquisition circuit that may be used with embodiments of the present invention.

FIG. 10 illustrates a further alternative signal acquisition circuit that may be used with embodiments of the present invention to select, from among a plurality of ECG sensing electrodes, those pairing of electrodes that provide a desired ECG signal, in terms of signal-to-noise ratio, phase discrimination, or any other criteria, and provide those ECG signals to downstream circuitry for further signal conditioning, processing, analysis, and/or monitoring. In contrast to the embodiments described previously with respect to FIGS. 2A-C and 3, and in a manner similar to the embodiment of FIG. 9, the signal acquisition circuit 1000 does not include any differential amplifiers, but instead generates differential ECG signals corresponding to selected pairings of ECG sensing electrodes in software executed by a processor, such as the at least one processor 410 described previously with respect to FIG. 4.

As shown, the signal acquisition circuit 1000 includes a plurality of analog-to-digital (A/D) converters 1010*a-p*. Each of the plurality of A/D converters 1010*a-p* is configured to receive a signal from a respective one of the plurality of ECG sensing electrodes 10*a-p*, for example, with a first A/D converter 1010*a* receiving a signal from ECG sensing electrode 10*a*, A/D converter 1010*b* receiving a signal from ECG sensing electrode 10*b*, etc. Each respective A/D converter 1010*a-p* converts the signal to a digital signal and provides the converted digital signal to the at least one processor 410 over a communication link 1020, such as a serial or parallel bus. Although not shown in FIG. 10, each of the signals from a respective ECG sensing electrode 10-10*p* may first be buffered, filtered, and/or amplified prior to being received at a respective input of a respective A/D converter 1010*a-p* in a manner similar to that described above with respect to FIG. 9 so that the A/D converter does not load down the respective ECG sensing electrode, and to ensure that any frequency components of the received signals are below the Nyquist frequency of a respective A/D converter 1010*a-p*.

To ensure adequate resolution for the processing performed by the at least one processor 410, each of the plurality of A/D converters 1010*a-p* may be a 24 bit A/D converter, although an A/D converter with fewer bits may be used. In contrast to the embodiment described above with respect to FIG. 9, each of plurality of A/D converters 1010*a-p* of this embodiment need not have a sampling rate that is N times the desired sampling rate of the ECG signal, where N is the number of ECG sensing electrodes that are desired to be monitored, because each of the signals received from a respective ECG sensing electrode may be sampled in parallel. For example, where it is desired to monitor ECG signals provided by each of three pairs of ECG sensing electrodes at a sampling rate of 400 Hz, each of the plurality of A/D converters may have a sampling rate of 400 Hz, thereby allowing the use of less costly A/D converters. Of course, it should be appreciated that higher sampling rates may be used. In accordance with this embodiment, the at least one processor 410 may send a control signal to each of the plurality of A/D converters 1010*a-p* to sample a respective signal at substantially the same period of time, and then send the sampled and converted digital signal to the processor at a subsequent time. Dependent upon which of the plurality of ECG sensing electrodes are selected to be paired with one another, the at least one processor takes the two selected digital signals, inverts one of them, and digitally sums the signals, effectively performing the same functionality as the differential instrumentation amplifiers described with respect to FIGS. 2A-C and 3 above. The selection, inversion, and summing of selected pairs of digital signals may again be performed for any pairing of ECG sensing electrodes. The digitally summed signals may then be processed to monitor the patient's ECG signals and/or to detect any arrhythmic cardiac condition.

FIG. 11 illustrates yet a further alternative signal acquisition circuit that may be used with embodiments of the present invention to select, from among a plurality of ECG sensing electrodes, those pairing of electrodes that provide a desired ECG signal, in terms of signal-to-noise ratio, phase discrimination, or any other criteria, and provide those ECG signals to downstream circuitry for further signal conditioning, processing, analysis, and/or monitoring. This embodiment is similar to the embodiment described above with respect to FIGS. 9 and 10 in that it again does not include any differential amplifiers, but instead generates differential ECG signals corresponding to selected pairings of ECG sensing electrodes in software executed by a processor, such as the at least one processor 410 described previously with respect to FIG. 4.

As in the embodiment described above with respect to FIG. 10, the signal acquisition circuit 1100 shown in FIG. 11 again includes a plurality of analog-to-digital (A/D) converters 1110a-p, each of which is configured to receive a signal from a respective one of the plurality of ECG sensing electrodes 10a-p. Although not shown in FIG. 11, each of the signals from a respective ECG sensing electrode 10-10p may first be buffered, filtered, and/or amplified prior to being received at a respective input of a respective A/D converter 1110a-p in a manner similar to that described above with respect to FIGS. 9 and 10 so that the A/D converter does not load down the respective ECG sensing electrode, and to ensure that any frequency components of the received signal are below the Nyquist frequency of a respective A/D converter 1110a-p.

In contrast to the embodiment of FIG. 10 in which the plurality of A/D converters 1010a-p are arranged in parallel, each of the plurality of A/D converters 1110a-p of this embodiment are daisy chained (or cascaded) to one another, for example via a serial bus, such as a SPI™ serial bus, a QSPI™ serial bus, or Microwire™ serial bus. Each respective A/D converter 1110a-p is arranged to sample a signal from a respective one of the plurality of ECG sensing electrodes 10a-p during a first time interval, and convert the signal to a digital signal and provide the converted digital signal to the next A/D converter in the chain during a subsequent time interval. The output of the last A/D converter 1110p in the chain is communicatively coupled to the at least one processor via a communication link 1120, such as a serial bus. The output of the last A/D converter in the chain (e.g., A/D converter 1110p) therefore provides a multi-bit signal to the at least one processor 410 with different bits in the multi-bit signal corresponding to different ECG sensing electrodes, for example, with a first series of bits corresponding to the converted digital signal obtained from ECG sensing electrode 10p, the second series of bits corresponding to the converted digital signal obtained from ECG sensing electrode 10o, and the last series of bits corresponding to the converted digital signal obtained from ECG sensing electrode 10a.

To ensure adequate resolution, each of the plurality of A/D converters 1110a-p may be a 24 bit A/D converter, although an A/D converter with fewer bits, such as 16 bits may alternatively be used. In contrast to the embodiment described above with respect to FIG. 9, and similar to the embodiment described above with respect to FIG. 10, each of plurality of A/D converters 1110a-p of this embodiment need not have a sampling rate that is N times the desired sampling rate of the ECG signal, where N is the number of ECG sensing electrodes that are desired to be monitored, because each of the signals received from a respective ECG sensing electrode may be sampled in parallel. Thus, where it is desired to monitor ECG signals provided by each of three pairs of ECG sensing electrodes at a particular sampling rate, each of the plurality of A/D converters may operate at that same sampling rate, thereby allowing the use of less costly A/D converters. However, because the plurality of A/D converters 1110a-p are daisy chained together, the rate at which the converted digital signals are communicated from one A/D converter to the next, and then to the at least one processor 410 should be at least N times the desired sampling rate of the ECG signal, where N corresponds to the number of ECG sensing electrodes that are desired to be monitored. A suitable type of A/D converter that can be cascaded or daisy chained in the manner described above is a MAX 11040K (24 bit) or Max11060 (16 bit) ADC available from Maxim Integrated Products of Sunnyvale Calif., although other analog-to digital converters available from other companies may alternatively be used.

In accordance with this embodiment, the at least one processor 410 may send a control signal to each of the plurality of A/D converters 1110a-p to sample a respective signal at substantially the same period of time, and send the sampled and converted digital signal to the next A/D converter in the chain, at a subsequent time. Ultimately, the last A/D converter 1110p provides the serial bitstream to the at least one processor 410. Dependent upon which of the plurality of ECG sensing electrodes are selected to be paired with one another, the at least one processor 410 extracts the digital signals corresponding to the two selected digital signals (typically corresponding to the same time period), inverts one of them, and digitally sums the signals, effectively performing the same functionality as the differential instrumentation amplifiers described with respect to FIGS. 2A-C and 3 above. The selection, inversion, and summing of selected pairs of digital signals may be performed for any pairing of ECG sensing electrodes, and corresponding to the same, or different time periods. The digitally summed signals may then be processed to monitor the patient's ECG signals and/or to detect any arrhythmic cardiac condition.

It should be appreciated that where the signal acquisition circuits described above with respect to FIGS. 9-11 are used with an electrode system associated with a wearable ambulatory medical device, each of these signal acquisition circuits not only permit the monitoring and analysis of ECG signals from any pairing of ECG sensing electrodes that are associated with the wearable ambulatory medical device, but they also permit the signal of any of the plurality of ECG sensing electrodes 10a-p to be paired with the signal from another source, such as a wireless ECG sensing electrode. For example, a wireless ECG sensing electrode may be provided that includes an A/D converter, such as any of A/D converters 1010a-p or 1110a-p described above, that is coupled to a wireless transmitter or transceiver and can communicate with the at least one processor 410 via a wireless communication protocol such as Bluetooth, ZigBee, Wireless USB, Wireless Ethernet, GSM, etc. The signal from the wireless ECG sensing electrode may then be paired with any of the signals from each of ECG sensing electrodes 10-p that are associated with the wearable ambulatory medical device, where it is desirable to do so. In this manner, if additional cardiac information is desired, additional wireless ECG sensing electrodes may be placed on the patient's body, and those signals monitored and analyzed. Indeed, in some embodiments, each of the ECG sensing electrodes need not be associated with a garment that is worn by the patient, but each of the ECG sensing electrodes may be self adhesive wireless ECG sensing electrodes that are simply placed, as desired, on the patient's body.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. An ambulatory medical device, comprising:
   a garment to be worn about a body of a patient;
   a plurality of electrodes configured to be attached to the garment and disposed at spaced apart positions about the body of the patient;
   an electrode signal acquisition circuit having a plurality of inputs, each respective input of the plurality of inputs being electrically coupled to a respective electrode of the plurality of electrodes, the electrode signal acquisition circuit being configured to sense a respective signal provided by each of a plurality of different pairings of the plurality of electrodes; and
   a monitoring circuit, electrically coupled to an output of the electrode signal acquisition circuit, the monitoring circuit being configured to analyze the respective signal provided by each of the plurality of different pairings and to instruct the electrode signal acquisition circuit to select at least one of the plurality of different pairings to monitor based upon at least two of a quality of the respective signal provided by the selected at least one of the plurality of different pairings, a phase difference between the respective signal provided by the selected at least one of the plurality of different pairings and the respective signal provided by another selected at least one of the plurality of different pairings, a position of the respective electrodes of the selected at least one of the plurality of different pairings relative to the body of the patient, and a plane defined by the respective electrodes of the selected at least one of the plurality of different pairings.

2. The ambulatory medical device of claim 1, wherein the plurality of electrodes are distributed about the torso of the patient.

3. The ambulatory medical device of claim 2, wherein the plurality of electrodes are ECG sensing electrodes, and wherein the monitoring circuit is a cardiac monitoring and arrhythmia detection circuit.

4. The ambulatory medical device of claim 3, wherein the plurality of ECG sensing electrodes includes at least three ECG sensing electrodes.

5. The ambulatory medical device of claim 4, wherein the plurality of ECG sensing electrodes are not all located in a common plane.

6. The ambulatory medical device of claim 5, further comprising:
   a plurality of therapy electrodes integrated into the garment and configured to deliver a defibrillating shock to the body of the patient in response to detection of a treatable cardiac arrhythmia by the cardiac monitoring and arrhythmia detection circuit.

7. The ambulatory medical device of claim 1, wherein the monitoring circuit is configured to select at least three of the plurality of different pairings to monitor based upon the at least two of the quality of the respective signal provided by each of the selected at least three of the plurality of different pairings, the phase difference between the respective signal provided by each of the selected at least three of the plurality of different pairings, the position of the respective electrodes of the selected at three of the plurality of different pairings relative to the body of the patient, and the plane defined by the respective electrodes of the selected at least three of the plurality of different pairings.

8. The ambulatory medical device of claim 1, wherein the plurality of electrodes includes at least four ECG sensing electrode that are not all located in a common plane.

9. The ambulatory medical device of claim 8, wherein the monitoring circuit is configured to select at least three of the plurality of different pairings to monitor based upon the at least two of the quality of the respective signal provided by each of the selected at least three of the plurality of different pairings, the phase difference between the respective signal provided by each of the selected at least three of the plurality of different pairings, the position of the respective electrodes of the selected at three of the plurality of different pairings relative to the body of the patient, and the plane defined by the respective electrodes of the selected at least three of the plurality of different pairings.

10. The ambulatory medical device of claim 9, wherein the monitoring circuit is configured to select at least two of the selected at least three of the plurality of different pairings to monitor during a first time interval and to select a different at least two of the selected at least three of the plurality of different pairings to monitor during a second time interval.

11. The ambulatory medical device of claim 1, wherein the electrode signal acquisition circuit includes:
   a plurality of differential amplifiers each having a pair of inputs and an output, the plurality of differential amplifiers including a respective differential amplifier for each unique pairing of the plurality of electrodes; and
   a selection circuit configured to select at least one output of the plurality of differential amplifiers to provide to the monitoring circuit.

12. A method of monitoring ECG signals, the method comprising acts of:
   selecting, from among a plurality of ECG sensors attached to a garment configured to be worn about a body of a patient, a plurality of different pairings of ECG sensors;
   analyzing a respective ECG signal provided by each of the plurality of different pairings;
   identifying at least one of the plurality of different pairings to monitor based upon at least two of a quality of the respective ECG signal provided by the identified at least one of the plurality of different pairings, a phase difference between the respective ECG signal provided by the identified at least one of the plurality of different pairings and the respective ECG signal provided by another identified at least one of the plurality of different pairings, a position of respective ECG sensors of the identified at least one of the plurality of different pairings relative to the body of the patient, and a plane defined by the respective ECG sensors of the identified at least one of the plurality of different pairings; and
   monitoring the identified at least one of the plurality of different pairings.

13. The ambulatory medical device of claim 1, wherein the monitoring circuit is further configured to select the at least one of the plurality of different pairings to monitor based upon a cardiac cycle of a heart of the patient.

14. The method of claim 12, wherein the act of selecting the plurality of different pairings of ECG sensors from among the plurality of ECG sensors includes an act of selecting, from among the plurality of ECG sensors, each unique pairing of ECG sensors; and wherein the act of analyzing the respective ECG signal provided by each of the plurality of different pairings includes analyzing the respective ECG signal provided by each unique pairing of ECG sensors.

15. The method of claim 14, wherein the act of monitoring includes:
    monitoring the identified at least one of the plurality of different pairings to detect a cardiac arrhythmia.

16. The method of claim 15, further comprising acts of:
    detecting the cardiac arrhythmia responsive to the act of monitoring;
    determining that the detected cardiac arrhythmia is a type of cardiac arrhythmia that can be treated by applying defibrillation to the body of the patient; and
    applying at least one defibrillation pulse to the body of the patient.

17. The method of claim 15, further comprising acts of:
    detecting the cardiac arrhythmia responsive to the act of monitoring;
    selecting at least one additional pairing of ECG sensors in response to detecting the cardiac arrhythmia and analyzing the respective ECG signal provided by the at least one additional pairing;
    determining that the detected cardiac arrhythmia is also present on the respective ECG signal of the at least one additional pairing;
    determining that the detected cardiac arrhythmia is a type of cardiac arrhythmia that can be treated by applying defibrillation to the body of the patient; and
    applying at least one defibrillation pulse to the body of the patient.

18. The method of claim 15, further comprising acts of:
    detecting the cardiac arrhythmia responsive to the act of monitoring;
    selecting at least one additional pairing of ECG sensors in response to detecting the cardiac arrhythmia and analyzing the respective ECG signal provided by the at least one additional pairing;
    determining that the detected cardiac arrhythmia is also present on the respective ECG signal of the at least one additional pairing; and
    increasing a confidence level that the cardiac arrhythmia has been detected.

19. The method of claim 15, further comprising acts of:
    detecting the cardiac arrhythmia responsive to the act of monitoring;
    selecting at least one additional pairing of ECG sensors in response to detecting the cardiac arrhythmia and analyzing the respective ECG signal provided by the at least one additional pairing;
    determining that the detected cardiac arrhythmia is not present on the respective ECG signal of the at least one additional pairing; and
    decreasing a confidence level that the cardiac arrhythmia has been detected.

20. The method of claim 12, wherein the acts of selecting, analyzing, and identifying are repeated at periodic intervals.

21. The method of claim 12, wherein the acts of selecting, analyzing, and identifying are performed each time the garment is placed about the body of the patient.

22. The method of claim 12, the method further comprising an act of:
    detecting strenuous physical activity of the patient; and
    repeating the acts of selecting, analyzing, and identifying in response to the act of detecting the strenuous activity of the patient.

23. The method of claim 12, wherein the act of identifying further includes identifying the at least one of the plurality of pairings to monitor based upon a cardiac cycle of a heart of the patient.

* * * * *